(12) United States Patent
Sepetka et al.

(10) Patent No.: US 8,771,294 B2
(45) Date of Patent: Jul. 8, 2014

(54) ANEURYSM TREATMENT DEVICES AND METHODS

(75) Inventors: Ivan Sepetka, Los Altos, CA (US);
Maria Aboytes, Palo Alto, CA (US);
Maybelle Jordan, Potomac, MD (US);
Craig Friedman, Westport, CT (US);
Arindam Datta, Hillsboro, NJ (US)

(73) Assignee: Biomerix Corporation, New York, NY (US)

( * ) Notice: Subject to any disclaimer, the term of this patent is extended or adjusted under 35 U.S.C. 154(b) by 275 days.

(21) Appl. No.: 11/111,487

(22) Filed: Apr. 21, 2005

(65) Prior Publication Data

US 2006/0116712 A1    Jun. 1, 2006

Related U.S. Application Data

(63) Continuation-in-part of application No. 10/998,357, filed on Nov. 26, 2004, now abandoned.

(51) Int. Cl.
*A61B 17/04* (2006.01)

(52) U.S. Cl.
USPC .......................................................... 606/144

(58) Field of Classification Search
USPC ................................... 606/144; 424/426, 144
See application file for complete search history.

(56) References Cited

U.S. PATENT DOCUMENTS

| | | |
|---|---|---|
| 1,896,071 A | 2/1933 | Clark |
| 2,546,754 A | 3/1951 | Jones |
| 2,616,422 A | 11/1952 | Jones |
| 3,175,025 A | 3/1965 | Geen et al. |
| 3,297,803 A * | 1/1967 | Meisel, Jr. et al. ............... 264/84 |
| 3,334,629 A | 8/1967 | Cohn |
| 3,562,352 A * | 2/1971 | Nyilas ....................... 525/440.04 |
| 4,459,252 A | 7/1984 | MacGregor |
| 4,689,386 A | 8/1987 | Chapman et al. |
| 4,890,612 A | 1/1990 | Kensey |
| 4,985,467 A | 1/1991 | Kelly et al. |
| 4,994,069 A | 2/1991 | Ritchart et al. |
| 5,061,274 A | 10/1991 | Kensey |
| 5,070,172 A | 12/1991 | Hirai et al. |
| 5,108,407 A | 4/1992 | Geremia |
| 5,120,816 A | 6/1992 | Gould et al. |
| 5,133,742 A | 7/1992 | Pinchuk |
| 5,229,431 A | 7/1993 | Pinchuk |
| 5,261,916 A | 11/1993 | Engelson |
| 5,284,488 A * | 2/1994 | Sideris .......................... 606/213 |

(Continued)

FOREIGN PATENT DOCUMENTS

| | | |
|---|---|---|
| EP | 0778005 | 6/1997 |
| EP | 0820726 | 9/2003 |

(Continued)

*Primary Examiner* — Gregory Anderson
(74) *Attorney, Agent, or Firm* — Pillsbury Winthrop Shaw Pittman, LLP

(57) ABSTRACT

An aneurysm treatment device for in situ treatment of aneurysms comprises a collapsible member having a first shape wherein the first shape is an expanded geometric configuration, and a second shape, wherein the second shape is a collapsed configuration that is loadable into a catheter. The aneurysm treatment device is capable or returning to the first shape in the sac of an aneurysm upon deployment, where it occludes the aneurysm. In another embodiment an occlusion device comprises a flexible, longitudinally extending elastomeric matrix member that assumes a non-linear shape to conformally fill a targeted vascular site.

32 Claims, 12 Drawing Sheets
(1 of 12 Drawing Sheet(s) Filed in Color)

(56) References Cited

U.S. PATENT DOCUMENTS

| | | |
|---|---|---|
| 5,296,518 A | 3/1994 | Grasel et al. |
| 5,308,342 A | 5/1994 | Sepetka et al. |
| 5,312,415 A | 5/1994 | Palermo |
| 5,334,210 A | 8/1994 | Gianturco |
| 5,354,295 A | 10/1994 | Guglielmi et al. |
| 5,382,259 A | 1/1995 | Phelps et al. |
| 5,417,708 A * | 5/1995 | Hall et al. ............ 606/200 |
| 5,423,849 A | 6/1995 | Engelson et al. |
| 5,514,085 A | 5/1996 | Yoon |
| 5,514,378 A | 5/1996 | Mikos et al. |
| 5,522,895 A | 6/1996 | Mikos |
| 5,562,698 A | 10/1996 | Parker |
| 5,582,619 A | 12/1996 | Ken |
| 5,607,474 A | 3/1997 | Athanasiou et al. |
| 5,658,308 A | 8/1997 | Snyder |
| 5,690,671 A | 11/1997 | McGurk et al. |
| 5,709,934 A | 1/1998 | Bell et al. |
| 5,725,546 A | 3/1998 | Samson |
| 5,741,297 A * | 4/1998 | Simon ............ 606/213 |
| 5,741,331 A | 4/1998 | Pinchuk |
| 5,749,894 A | 5/1998 | Engelson |
| 5,755,774 A * | 5/1998 | Pinchuk ............ 623/1.13 |
| 5,770,193 A | 6/1998 | Vacanti et al. |
| 5,776,184 A | 7/1998 | Tuch |
| 5,800,455 A | 9/1998 | Palermo |
| 5,823,198 A | 10/1998 | Jones et al. |
| 5,824,081 A | 10/1998 | Knapp et al. |
| 5,833,705 A | 11/1998 | Ken et al. |
| 5,843,118 A | 12/1998 | Sepetka et al. |
| 5,853,418 A | 12/1998 | Ken et al. |
| 5,863,627 A | 1/1999 | Szycher |
| 5,891,192 A | 4/1999 | Murayama et al. |
| 5,891,558 A | 4/1999 | Bell et al. |
| 5,895,407 A | 4/1999 | Jayaraman |
| 5,904,703 A | 5/1999 | Gilson |
| 5,925,060 A | 7/1999 | Forber |
| 6,015,424 A | 1/2000 | Rosenbluth et al. |
| 6,024,754 A | 2/2000 | Engelson |
| 6,033,423 A | 3/2000 | Ken et al. |
| 6,034,149 A | 3/2000 | Bleys et al. |
| 6,042,592 A | 3/2000 | Schmitt |
| 6,054,142 A | 4/2000 | Li et al. |
| 6,066,133 A | 5/2000 | Guglielmi |
| 6,066,776 A | 5/2000 | Goodwin et al. |
| 6,083,220 A | 7/2000 | Guglielmi |
| 6,102,932 A | 8/2000 | Kurz |
| 6,102,939 A | 8/2000 | Pinchuk |
| 6,111,052 A | 8/2000 | DiDomenico et al. |
| 6,113,629 A | 9/2000 | Ken |
| 6,136,015 A | 10/2000 | Kurz et al. |
| 6,149,664 A | 11/2000 | Kurz |
| 6,149,678 A | 11/2000 | DiDomenico et al. |
| 6,153,292 A | 11/2000 | Bell et al. |
| 6,159,165 A | 12/2000 | Ferrera et al. |
| 6,165,193 A | 12/2000 | Greene, Jr. et al. |
| 6,165,212 A | 12/2000 | Dereume et al. |
| 6,168,592 B1 | 1/2001 | Kupiecki et al. |
| 6,168,622 B1 | 1/2001 | Mazzocchi |
| 6,177,522 B1 | 1/2001 | Brady et al. |
| 6,187,027 B1 | 2/2001 | Mariant et al. |
| 6,221,066 B1 | 4/2001 | Ferrera et al. |
| 6,224,630 B1 | 5/2001 | Bao et al. |
| 6,231,586 B1 | 5/2001 | Mariant |
| 6,231,590 B1 | 5/2001 | Slaikeu et al. |
| 6,231,879 B1 | 5/2001 | Li et al. |
| 6,238,403 B1 | 5/2001 | Greene, Jr. et al. |
| 6,245,090 B1 | 6/2001 | Gilson et al. |
| 6,245,107 B1 | 6/2001 | Ferree |
| 6,280,457 B1 | 8/2001 | Wallace et al. |
| 6,299,619 B1 | 10/2001 | Greene, Jr. et al. |
| 6,306,424 B1 | 10/2001 | Vyakarnam et al. |
| 6,309,413 B1 | 10/2001 | Dereume et al. |
| 6,312,421 B1 | 11/2001 | Boock |
| 6,313,254 B1 | 11/2001 | Meijs et al. |
| 6,322,576 B1 | 11/2001 | Wallace et al. |
| 6,333,029 B1 | 12/2001 | Vyakarnam et al. |
| 6,335,384 B1 | 1/2002 | Evans et al. |
| 6,344,048 B1 | 2/2002 | Chin et al. |
| 6,355,699 B1 | 3/2002 | Vyakarnam et al. |
| 6,365,149 B2 | 4/2002 | Vyakarnam et al. |
| 6,368,338 B1 | 4/2002 | Konya et al. |
| 6,375,662 B1 | 4/2002 | Schmitt |
| 6,375,668 B1 | 4/2002 | Gifford et al. |
| 6,375,669 B1 | 4/2002 | Rosenbluth et al. |
| 6,409,721 B1 | 6/2002 | Wheelock |
| 6,420,452 B1 | 7/2002 | Gunatillake et al. |
| 6,428,558 B1 | 8/2002 | Jones et al. |
| 6,432,122 B1 | 8/2002 | Gilson et al. |
| 6,437,073 B1 | 8/2002 | Gunatilake et al. |
| 6,454,811 B1 | 9/2002 | Sherwood et al. |
| 6,458,127 B1 | 10/2002 | Truckai et al. |
| 6,500,190 B2 | 12/2002 | Greene, Jr. et al. |
| 6,514,280 B1 | 2/2003 | Gilson |
| 6,545,097 B2 | 4/2003 | Pinchuk et al. |
| 6,599,323 B2 | 7/2003 | Melican et al. |
| 6,602,261 B2 | 8/2003 | Greene, Jr. et al. |
| 6,605,101 B1 | 8/2003 | Schaefer et al. |
| 6,616,617 B1 | 9/2003 | Ferrera et al. |
| 6,617,014 B1 | 9/2003 | Thomson |
| 6,638,293 B1 | 10/2003 | Makower et al. |
| 6,638,312 B2 | 10/2003 | Plouhar et al. |
| 6,656,201 B2 | 12/2003 | Ferrera et al. |
| 6,669,706 B2 | 12/2003 | Schmitt et al. |
| 6,673,285 B2 | 1/2004 | Ma |
| 6,692,510 B2 | 2/2004 | West |
| 6,723,108 B1 | 4/2004 | Jones et al. |
| 6,723,112 B2 | 4/2004 | Ho et al. |
| 6,852,330 B2 | 2/2005 | Bowman et al. |
| 6,872,218 B2 | 3/2005 | Ferrera et al. |
| 6,884,428 B2 | 4/2005 | Binette et al. |
| 6,966,892 B2 | 11/2005 | Gandhi et al. |
| 7,029,487 B2 | 4/2006 | Greene |
| 7,033,388 B2 | 4/2006 | Zilla et al. |
| 7,070,584 B2 * | 7/2006 | Johnson et al. ............ 604/313 |
| 7,112,417 B2 | 9/2006 | Vyakarnam et al. |
| 7,803,395 B2 | 9/2010 | Datta et al. |
| 2002/0018884 A1 | 2/2002 | Thomson |
| 2002/0072550 A1 | 6/2002 | Brady et al. |
| 2002/0119177 A1 | 8/2002 | Bowman et al. |
| 2002/0120348 A1 | 8/2002 | Melican et al. |
| 2002/0138095 A1 | 9/2002 | Mazzocchi et al. |
| 2002/0142413 A1 | 10/2002 | Brady et al. |
| 2002/0169497 A1 | 11/2002 | Wholey et al. |
| 2002/0169499 A1 | 11/2002 | Zilla et al. |
| 2003/0014075 A1 | 1/2003 | Rosenbluth et al. |
| 2003/0130689 A1 | 7/2003 | Wallace et al. |
| 2003/0171773 A1 | 9/2003 | Carrison |
| 2003/0193104 A1 | 10/2003 | Melican |
| 2003/0199887 A1 | 10/2003 | Ferrera et al. |
| 2003/0204246 A1 | 10/2003 | Chu et al. |
| 2004/0078077 A1 | 4/2004 | Binette et al. |
| 2004/0087834 A1 | 5/2004 | Benetti et al. |
| 2004/0098024 A1 | 5/2004 | Dieck et al. |
| 2004/0115164 A1 | 6/2004 | Pierce et al. |
| 2004/0158282 A1 | 8/2004 | Jones et al. |
| 2004/0161451 A1 | 8/2004 | Pierce et al. |
| 2004/0175408 A1 | 9/2004 | Chun et al. |
| 2005/0021023 A1 | 1/2005 | Guglielmi |
| 2005/0021077 A1 | 1/2005 | Chin et al. |
| 2005/0043585 A1 | 2/2005 | Datta et al. |
| 2005/0043816 A1 | 2/2005 | Datta et al. |
| 2005/0149046 A1 | 7/2005 | Friedman et al. |
| 2006/0052814 A1 | 3/2006 | Sater |
| 2007/0003594 A1 * | 1/2007 | Brady et al. ............ 424/426 |

FOREIGN PATENT DOCUMENTS

| | | |
|---|---|---|
| EP | 0274898 | 12/2005 |
| WO | WO 93/06854 | 4/1993 |
| WO | WO 94/06460 | 3/1994 |
| WO | WO 94/07560 | 4/1994 |
| WO | WO 99/23954 | 5/1999 |
| WO | WO 99/24084 | 5/1999 |
| WO | WO 99/61084 | 12/1999 |

(56) References Cited

FOREIGN PATENT DOCUMENTS

| WO | WO 00/67812 | 11/2000 |
| WO | WO 01/03607 | 1/2001 |
| WO | WO 01/05333 | 1/2001 |
| WO | WO 01/21108 | 3/2001 |
| WO | WO 2004/062531 | 7/2004 |
| WO | WO 2006/088531 | 8/2006 |

* cited by examiner

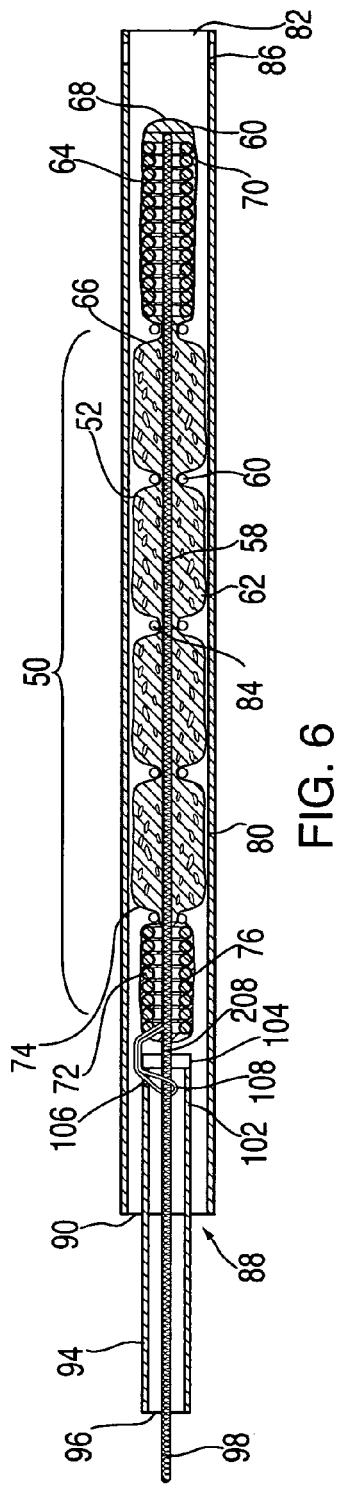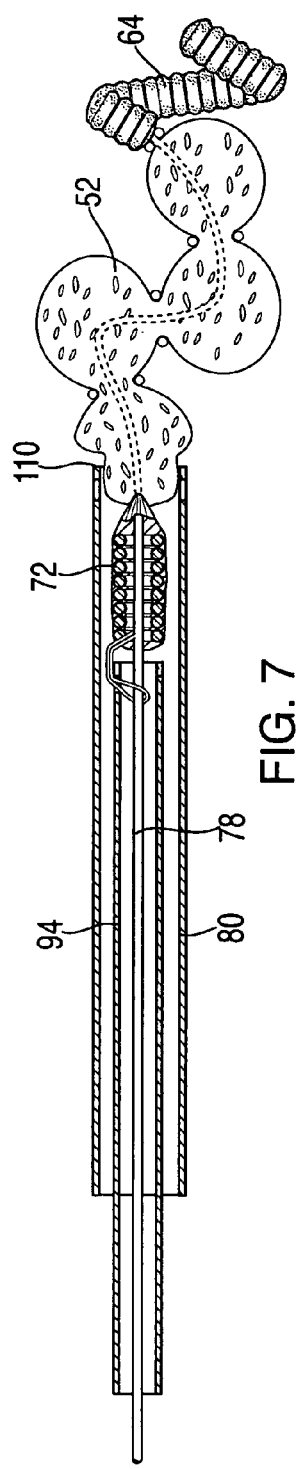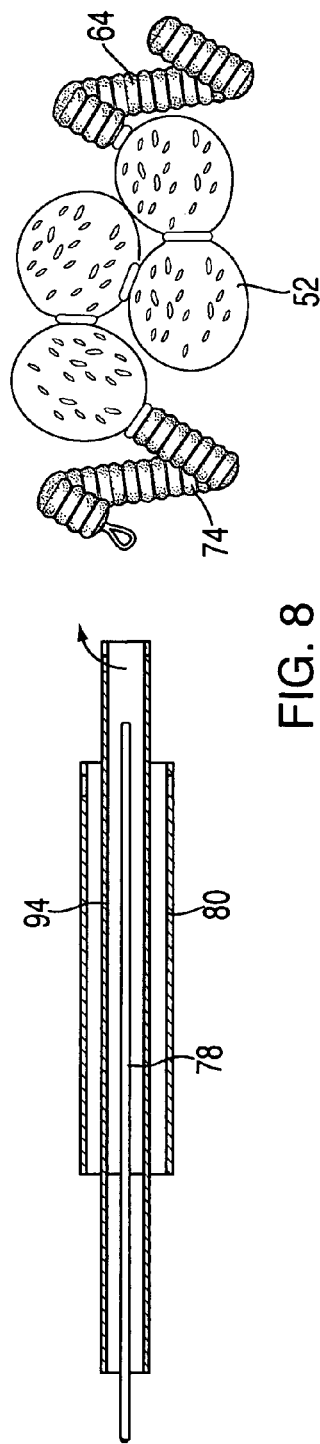

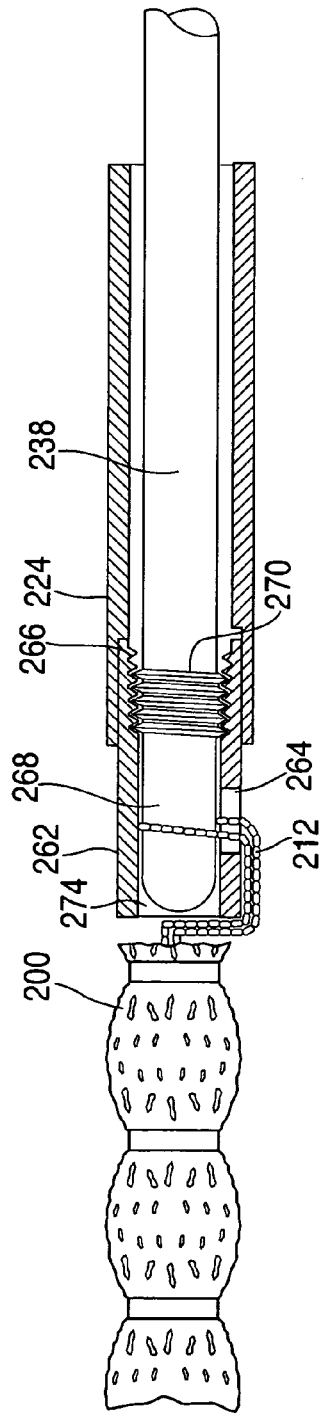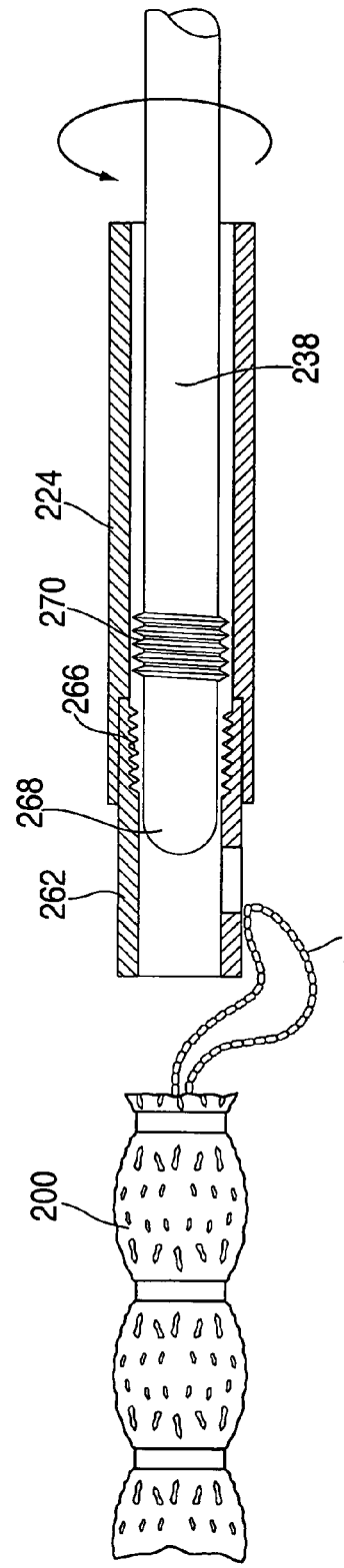
FIG. 18
FIG. 19

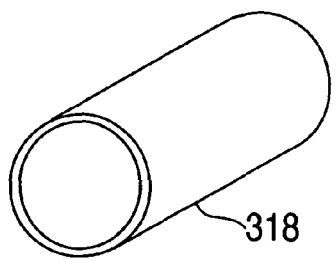 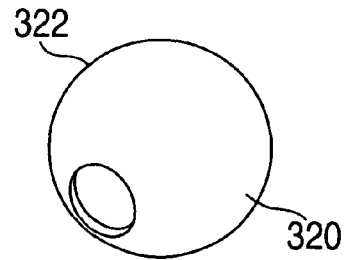
FIG. 22A            FIG. 22B
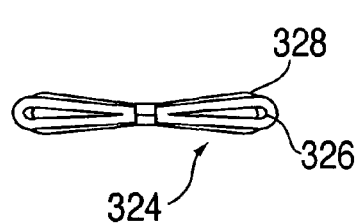 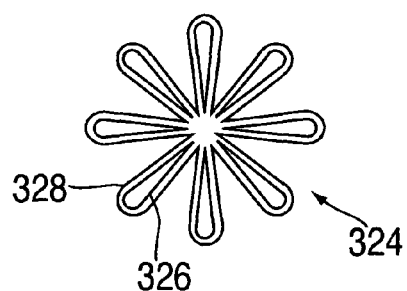
FIG. 23A            FIG. 23B
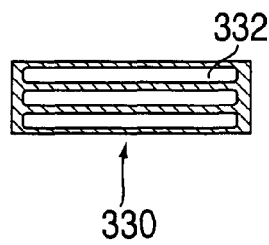 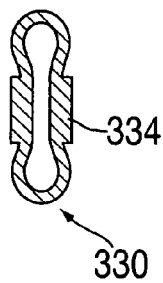
FIG. 24A            FIG. 24B

ANEURYSM TREATMENT DEVICES AND METHODS

CROSS-REFERENCE TO RELATED APPLICATION

This application is a continuation-in-part of commonly assigned U.S. patent application Ser. No. 10/998,357, filed Nov. 26, 2004 now abandoned, which is incorporated herein by reference.

FIELD OF THE INVENTION

This invention relates to methods and devices for the treatment of vascular aneurysms and other comparable vascular abnormalities. More particularly, this invention relates to occlusion devices for vascular aneurysms that comprise a reticulated elastomeric matrix structure and a delivery device.

BACKGROUND OF THE INVENTION

The cardio-vascular system, when functioning properly, supplies nutrients to all parts of the body and carries waste products away from these parts for elimination. It is essentially a closed-system comprising the heart, a pump that supplies pressure to move blood through the blood vessels, blood vessels that lead away from the heart, called arteries, and blood vessels that return blood toward the heart, called veins. On the discharge side of the heart is a large blood vessel called the aorta from which branch many arteries leading to all parts of the body, including the organs. As the arteries get close to the areas they serve, they diminish to small arteries, still smaller arteries called arterioles, and ultimately connect to capillaries. Capillaries are minute vessels where outward diffusion of nutrients, including oxygen, and inward diffusion of wastes, including carbon dioxide, takes place. Capillaries connect to tiny veins called venules.

Venules in turn connect to larger veins which return the blood to the heart by way of a pair of large blood vessels called the inferior and superior venae cava.

As shown in FIG. 1, arteries 2 and veins comprise three layers known as tunics. An inner layer 4, called the tunica interna, is thin and smooth, constituted of endothelium, and rests on a connective tissue membrane rich in elastic and collagenous fibers that secrete biochemicals to perform functions such as prevention of blood clotting by inhibiting platelet aggregation and regulation of vasoconstriction and vasodilation. A middle layer 6 called the tunica media is made of smooth muscle 8 and elastic connective tissue 10 and provides most of the girth of the blood vessel. A thin outer layer 12, called the tunica adventitia, formed of connective tissue secures the blood vessel to the surrounding tissue.

The tunica media 6 differentiates an artery from a vein in that it is thicker in an artery to withstand the higher blood pressure exerted by the heart on the walls of the arteries. Tough elastic connective tissue provides an artery 2 sufficient elasticity to withstand the blood pressure and sudden increases in blood volume that occur with ventricular contractions.

When the wall of an artery, especially the tunica media 6 of that wall, has a weakness, the blood pressure can dilate or expand the region of the artery 2 with the weakness, and a pulsating sac 14 called a berry or saccular aneurysm (FIG. 2), can develop. If the walls of the arteries 2 expand around the circumference of the artery 2, this is called a fusiform aneurysm 16 (FIG. 3). If the weakness causes a longitudinal tear in the tunica media of the artery, it is called a dissecting aneurysm. Saccular aneurysms are common at artery bifurcations 18 (FIGS. 4 and 5) located around the brain. Dissecting aneurysms are common in the thoracic and abdominal aortas. The pressure of an aneurysm against surrounding tissues, especially the pulsations, may cause pain and may also cause tissue damage. However, aneurysms are often asymptomatic. The blood in the vicinity of the aneurysm can become turbulent, leading to formation of blood clots, that may be carried to various body organs where they may cause damage in varying degrees, including cerebrovascular incidents, myocardial infarctions and pulmonary embolisms. Should an aneurysm tear and begin to leak blood, the condition can become life threatening, sometimes being quickly fatal, in a matter of minutes.

Because there is relatively little blood pressure in a vein, venous "aneurysms" are non-existent. Therefore, the description of the present invention is related to arteries, but applications within a vein, if useful, are to be understood to be within the scope of this invention.

The causes of aneurysms are still under investigation. However, researchers have identified a gene associated with a weakness in the connective tissue of blood vessels that can lead to an aneurysm. Additional risk factors associated with aneurysms such as hyperlipidemia, atherosclerosis, fatty diet, elevated blood pressure, smoking, trauma, certain infections, certain genetic disorders, such as Marfan's Syndrome, obesity, and lack of exercise have also been identified. Cerebral aneurysms frequently occur in otherwise healthy and relatively youthful people and have been associated with many untimely deaths.

Aneurysms, widening of arteries caused by blood pressure acting on a weakened arterial wall, have occurred ever since humans walked the planet. In recent times, many methods have been proposed to treat aneurysms. For example, Greene, Jr., et al., in U.S. Pat. No. 6,165,193 propose a vascular implant formed of a compressible foam hydrogel that has a compressed configuration from which it is expansible into a configuration substantially conforming to the shape and size of a vascular malformation to be embolized. Greene's hydrogel lacks the mechanical properties to enable it to regain its size and shape in vivo were it to be compressed for catheter, endoscope, or syringe delivery, and the process can be complex and difficult to implement. Other patents disclose introduction of a device, such as a stent or balloon (Naglreiter et al., U.S. Pat. No. 6,379,329) into the aneurysm, followed by introduction of a hydrogel in the area of the stent to attempt to repair the defect (Sawhney et al., U.S. Pat. No. 6,379,373).

Still other patents suggest the introduction into the aneurysm of a device, such as a stent, having a coating of a drug or other bioactive material (Gregory, U.S. Pat. No. 6,372,228). Other methods include attempting to repair an aneurysm by introducing via a catheter a self-hardening or self-curing material into the aneurysm. Once the material cures or polymerizes in situ into a foam plug, the vessel can be recanalized by placing a lumen through the plug (Hastings, U.S. Pat. No. 5,725,568).

Another group of patents relates more specifically to saccular aneurysms and teaches the introduction of a device, such as string, wire or coiled material (Boock U.S. Pat. No. 6,312,421), or a braided bag of fibers (Greenhalgh, U.S. Pat. No. 6,346,117) into the lumen of the aneurysm to fill the void within the aneurysm. The device introduced can carry hydrogel, drugs or other bioactive materials to stabilize or reinforce the aneurysm (Greene Jr. et al., U.S. Pat. No. 6,299,619).

Another treatment known to the art comprises catheter delivery of platinum microcoils into the aneurysm cavity in conjunction with an embolizing composition comprising a biocompatible polymer and a biocompatible solvent. The deposited coils or other non-particulate agents are said to act as a lattice about which a polymer precipitate grows thereby embolizing the blood vessel (Evans et al., U.S. Pat. No. 6,335, 384).

It is an understanding of the present invention that such methods and devices suffer a variety of problems. For example, if an aneurysm treatment is to be successful, any implanted device must be present in the body for a long period of time, and must therefore be resistant to rejection, and not degrade into materials that cause adverse side effects. While platinum coils may be having some benefits in this respect, they are inherently expensive, and the pulsation of blood around the aneurysm may cause difficulties such as migration of the coils, incomplete sealing of the aneurysm, or fragmentation of blood clots. It is also well known that the use of a coil is frequently associated with recanalization of the site, leading to full or partial reversal of the occlusion. If the implant does not fully occlude the aneurysm and effectively seal against the aneurysm wall, pulsating blood may seep around the implant and the distended blood vessel wall causing the aneurysm to reform around the implant.

The delivery mechanics of many of the known aneurysm treatment methods can be difficult, challenging, and time consuming.

Most contemporary vascular occlusion devices, such as coils, thrombin, glue, hydrogels, etc., have serious limitations or drawbacks, including, but not limited to, early or late recanalization, incorrect placement or positioning, migration, and lack of tissue ingrowth and biological integration. Also, some of the devices are physiologically unacceptable and engender unacceptable foreign body reactions or rejection. In light of the drawbacks of the known devices and methods, there is a need for more effective aneurysm treatment that produces permanent biological occlusion, can be delivered in a compressed state through small diameter catheters to a target vascular or other site with minimal risk of migration, will prevent the aneurysm from leaking or reforming.

OBJECTS OF THE INVENTION

It is an object of this invention to provide a method and device for the treatment of vascular aneurysms.

It is also an object of this invention to provide a method and device for occluding cerebral aneurysms.

It is a further object of the invention to provide a method and device for occluding cerebral aneurysms by bio-integrating and sealing off the aneurysm to prevent migration, recanalization, leaking, or reforming.

It is a yet further object of this invention to provide a method and device for occluding vascular aneurysms wherein the device comprises a reticulated elastomeric matrix structure and a delivery device.

It is a yet further object of this invention to provide a system for treating cerebral aneurysms that comprises a reticulated elastomeric matrix structure and a delivery device.

It is a yet further object of the invention to provide an implant for occluding a cerebral aneurysm that comprises a reticulated elastomeric matrix structure that compresses for delivery and expands upon deployment in an aneurysm to cause angiographic occlusion.

These and other objects of the invention will become more apparent in the discussion below.

SUMMARY OF THE INVENTION

According to the invention an aneurysm treatment device is provided for in situ treatment of aneurysms, particularly, cerebral aneurysms, in mammals, especially humans. The treatment device comprises a resiliently collapsible implant comprised of a reticulated, biodurable elastomeric matrix, which is collapsible from a first, expanded configuration wherein the implant can support the wall of an aneurysm to a second collapsed configuration wherein the collapsible implant is deliverable into the aneurysm, for example, by being loadable into a catheter and passed through the patient's vasculature. Pursuant to the invention, useful aneurysm treatment devices can have sufficient resilience, or other mechanical property, including expansion, to return to an expanded configuration within the space of the aneurysm and to occlude the aneurysm. Preferably, the implant is configured so that hydraulic forces within the aneurysm coupled with recovery and resilience characteristics of the reticulated elastomeric matrix tend to urge the implant against the aneurysm wall.

In another embodiment of the invention, an implant comprises one or more flexible, connected, preferably spherically-, ellipsoidally-, or cylindrically-shaped structures that are positioned in a compressed state in a delivery catheter. The connected structures preferably have spring coils on each end, one of which coils is releasably secured within the delivery catheter. A longitudinally extending rod or wire that acts to assist in pushing the implant distally extends through the structures and is withdrawn during delivery. The implant tends to form a spiral shape after delivery.

In another embodiment of the invention an implant that is initially essentially cylindrical in shape in connection with a delivery catheter comprises a mechanism such that when the structure is positioned at a desired location, the mechanism is engaged to cause the structure to assume any particular shape that will occlude an aneurysm.

In another embodiment of the invention, an implant for occlusion of an aneurysm comprises reticulated elastomeric matrix in a shape that can be compressed, can be inserted into a delivery catheter, can be ejected or deployed from the delivery catheter into an aneurysm, and can then expand to sufficient size and shape to occlude the aneurysm. Examples of such shapes include, but are not limited to, spheres, hollow spheres, cylinders, hollow cylinders, noodles, cubes, pyramids, tetrahedrons, hollow cylinders with lateral slots, trapezoids, parallelepipeds, ellipsoids, rods, tubes, or elongated prismatic forms, folded, coiled, helical or other more compact configurations, segmented cylinders where "sausage-like" segments have been formed, flat square or rectangular shapes, daisy shapes, braided shapes, or flat spiral shapes, optionally with surgical suture or radiopaque wire support extending therein.

Although multiple implants can be deployed, used or implanted, it is a feature of one aspect of the present invention that preferably a single implant fills an aneurysm, effectively a "single shot" occlusion. It is contemplated, in one embodiment, that even when their pores become partially filled or completely filled with biological fluids, bodily fluids and/or tissue in the course of time or immediately after delivery, and/or the implants are either still partially compressed or partially recovered after delivery, such implantable device or devices for vascular malformation applications have a volume of at least about 50% of the aneurysm volume. The ratio of implant (or implants) volume to aneurysm volume is defined as packing density. In another embodiment, such implantable device or devices for vascular malformation applications have a volume of at least about 75% of the aneurysm volume. In another embodiment, such implantable device or devices for vascular malformation applications have a volume of at least about 125% of the aneurysm volume. In another embodiment, such implantable device or devices for vascular malformation applications have a volume of at least about 175% of the aneurysm volume. In another embodiment, such implantable device or devices for vascular malformation applications have a volume of at least about 200% of the aneurysm volume. In another embodiment, such implantable device or devices for vascular malformation applications have a volume of at least about 300% of the aneurysm volume. In another embodiment, such implantable device or devices for vascular malformation applications have a volume of at least about 400% of the aneurysm volume.

The packing density is targeted to achieve angiographic occlusion after embolization of the aneurysm by the implant, followed by clotting, thrombosis, and tissue ingrowth, ultimately leading to biological obliteration of the aneurysm sac. Permanent tissue ingrowth will prevent any possible recanalization.

It is furthermore preferable that the implant be treated or formed of a material that will encourage such fibroblast immigration. It is also desirable that the implant be configured, with regard to its three-dimensional shape, and its size, resiliency and other physical characteristics, and be suitably chemically or biochemically constituted to foster eventual tissue ingrowth and formation of scar tissue that will help fill and/or obliterate the aneurysm sac.

The aneurysm treatment device preferably comprises a reticulated biodurable elastomeric matrix or the like that is capable of being compressed and inserted into a catheter for implantation. In another embodiment, the implant can be formed of a partially hydrophobic reticulated biodurable elastomeric matrix having its pore surfaces coated to be partially hydrophilic, for example, by being coated with at least a partially hydrophilic material, optionally a partially hydrophilic reticulated elastomeric matrix. Preferably the entire foam has such a hydrophilic coating throughout the pores of the reticulated elastomeric matrix.

In one embodiment, the hydrophilic material carries a pharmacologic agent, for example, elastin to foster fibroblast proliferation. It is also within the scope of the invention for the pharmacologic agent to include sclerotic agents, inflammatory induction agents, growth factors capable of fostering fibroblast proliferation, or genetically engineered an/or genetically acting therapeutics. The pharmacologic agent or agents preferably are dispensed over time by the implant. Incorporation of biologically active agents in the hydrophilic phase of a composite foam suitable for use in the practice of the present invention is described in co-pending, commonly assigned U.S. patent applications Ser. No. 10/692,055, filed Oct. 22, 2003, Ser. No. 10/749,742, filed Dec. 30, 2003, Ser. No. 10/848,624, filed May 17, 2004, and Ser. No. 10/900,982, filed Jul. 27, 2004, each of which is incorporated herein by reference in its entirety.

In another aspect, the invention provides a method of treating an aneurysm comprising the steps of:

imaging an aneurysm to be treated to determine its size and topography;

selecting an aneurysm treatment device according to the invention for use in treating the aneurysm; and implanting the aneurysm treatment device into the aneurysm.

Preferably, the method further comprises:

loading the aneurysm treatment device into a catheter or other delivery means;

threading the catheter through an artery to the aneurysm; and positioning and releasing the aneurysm treatment device in the aneurysm.

Once an aneurysm has been identified using suitable imaging technology, such as a magnetic resonance image (MRI), computerized tomography scan (CT Scan), x-ray imaging with contrast material or ultrasound, and is to be treated, the surgeon chooses which implant he or she feels would best suit the aneurysm, both in shape and size. The implant can be used alone. In another embodiment, the aneurysm treatment device of the invention may also be used in conjunction with a frame of platinum coils to assist in reducing or eliminating the risk of implant migration out of the neck of the aneurysm. This is particularly true in the case of wide neck or giant aneurysms. The chosen implant is then loaded into an intravascular catheter in a compressed state. If desired, the implant can be provided in a sterile package in a pre-compressed configuration, ready for loading into a catheter. Alternatively, the implants can be made available in an expanded state, also, preferably, in a sterile package, and the surgeon at the site of implantation can use a suitable secondary device or a loader apparatus to compress an implant so that it can be loaded into a delivery catheter.

With an implant loaded into the catheter, the catheter is advanced through an artery to the diseased portion of the affected artery using any suitable technique known in the art. By use of the catheter the implant is then inserted and positioned within the aneurysm. As the implant is released from the catheter, where it is in its compressed state, it expands and is manipulated into a suitable position within the aneurysm.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

One or more embodiments of the invention and of making and using the invention, as well as the best mode contemplated of carrying out the invention, are described in detail below, by way of example, with reference to the accompanying drawings, in which:

FIGS. 6 to 8 illustrate an embodiment of the invention wherein a segmented vascular occlusion device is deployed;

FIGS. 11 to 24B represent embodiments of implants and delivery systems useful according to the invention;

DETAILED DESCRIPTION OF THE INVENTION

Figure 1:
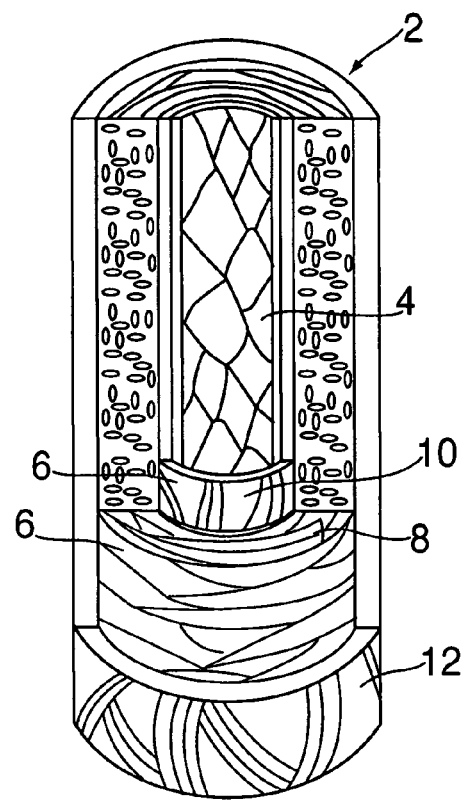
FIG. 1 is a side view of an artery with layers partially cut away to illustrate the anatomy of the artery.
Figure 4:
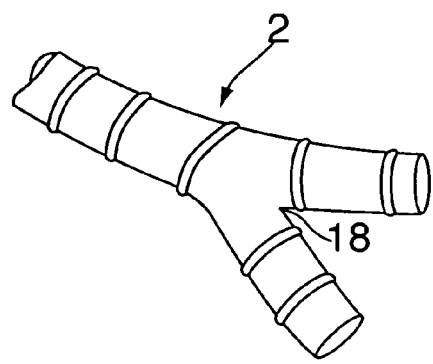
FIG. 4 is a top view of an artery at a bifurcation.
Figure 5:
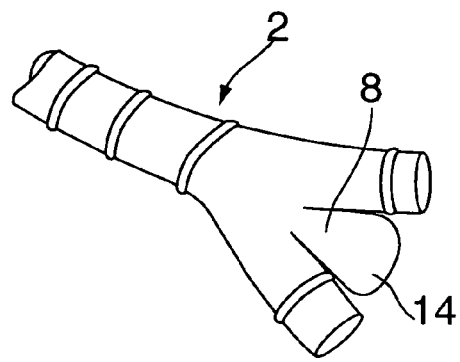
FIG. 5 is a top view of an artery at a bifurcation with a saccular aneurysm at the point of bifurcation.
Figure 2:
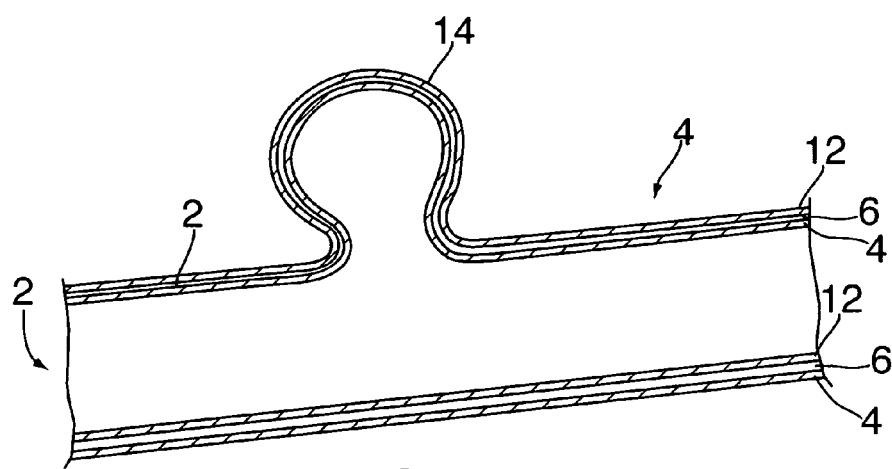
FIG. 2 is a longitudinal cross-section of an artery with a saccular aneurysm.
Figure 3:
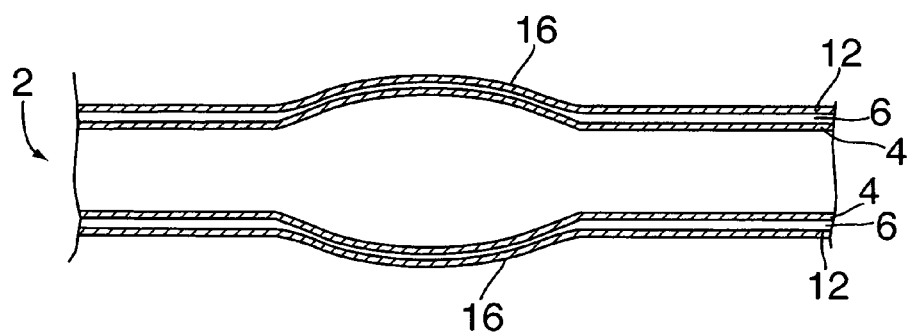
FIG. 3 is a longitudinal cross-section of an artery with a fusiform aneurysm.

The present invention relates to a system and method for treating aneurysms, particularly cerebral aneurysms, in situ. As will be described in detail below, the present invention provides an aneurysm treatment device comprising a reticulated, biodurable elastomeric matrix implant designed to be permanently inserted into an aneurysm with the assistance of an intravascular catheter. Reticulated matrix, from which the implants are made, has sufficient and required liquid permeability and thus selected to permit blood, or other appropriate bodily fluid, and cells and tissues to access interior surfaces of the implants. This happens due to the presence of inter-connected and inter-communicating, reticulated open pores and/or voids and/or channels that form fluid passageways or fluid permeability providing fluid access all through. The implants described in detail below can be made in a variety of sizes and shapes, the surgeon being able to choose the best size and shape to treat a patient's aneurysm. Once inserted the inventive aneurysm treatment device or implant is designed to cause angiographic occlusion, followed by clotting, thrombosis, and eventually bio-integration through tissue ingrowth and proliferation. Furthermore, the inventive aneurysm treatment device can carry one or more of a wide range of beneficial drugs and chemical moieties that can be released at the affected site for various treatments, such as to aid in healing, foster scarring of the aneurysm, prevent further damage, or reduce risk of treatment failure. With release of these drugs and chemicals locally, employing the devices and methods of the invention, their systemic side effects are reduced.

An implant or occlusion device according to the invention can comprise a reticulated biodurable elastomeric matrix or other suitable material and can be designed to be inserted into an aneurysm through a catheter. A preferred reticulated elastomeric matrix is a compressible, lightweight material, designed for its ability to expand within the aneurysm without expanding too much and tearing the aneurysm. Although multiple implants can be deployed, used or implanted, preferably a single implant should fill the aneurysm to achieve angiographic occlusion. It is contemplated, in one embodiment, that even when their pores become partially filled or completely filled with biological fluids, bodily fluids and/or tissue in the course of time or immediately after delivery, and/or the implants are either still partially compressed or partially recovered after delivery, such implantable device or devices for vascular malformation applications have a volume of at least about 50% of the aneurysm volume. The ratio of implant (or implants) volume to aneurysm volume is defined as packing density. In another embodiment, such implantable device or devices for vascular malformation applications have a volume of at least about 75% of the aneurysm volume. In another embodiment, such implantable device or devices for vascular malformation applications have a volume of at least about 125% of the aneurysm volume. In another embodiment, such implantable device or devices for vascular malformation applications have a volume of at least about 175% of the aneurysm volume. In another embodiment, such implantable device or devices for vascular malformation applications have a volume of at least about 200% of the aneurysm volume. In another embodiment, such implantable device or devices for vascular malformation applications have a volume of at least about 300% of the aneurysm volume. In another embodiment, such implantable device or devices for vascular malformation applications have a volume of at least about 400% of the aneurysm volume. Insertion of the implant followed by tissue ingrowth should result in total obliteration of the aneurysm sac.

Employment of an implant that can support invasion of fibroblasts and other cells enables the implant to eventually become a part of the healed aneurysm. Elastin can also be coated onto the implant providing an additional route of clot formation.

The implant can also contain one or more radiopaque markers for visualization by radiography or ultrasound to determine the orientation and location of the implant within the aneurysm sac. Preferably plantinum markers are incorporated in the implant and/or relevant positions of delivery members.

If desired, the outer surfaces of the implant or occlusion device can be coated, after fabrication of the implant or occlusion device with functional agents, such as those described herein, optionally employing an adjuvant that secures the functional agents to the surfaces and to reticulated elastomeric matrix pores adjacent the outer surfaces, where the agents will become quickly available. Such external coatings, which may be distinguished from internal coatings provided within and preferably throughout the pores of reticulated elastomeric matrix used, may comprise fibrin and/or other agents to promote fibroblast growth.

Once an aneurysm has been identified using suitable imaging technology, such as a magnetic resonance image (MRI), computerized tomography scan (CT Scan), x-ray imaging with contrast material or ultrasound, the surgeon chooses which implant he or she feels would best suit the aneurysm, both in shape and size. The chosen implant is then loaded into an intravascular catheter in a compressed state. The implants can be sold in a sterile package containing a pre-compressed implant that is loaded into a delivery catheter. Alternatively, the implant can be sold in a sterile package in an expanded state, and the surgeon at the site of implantation can use a device, e.g. a ring, funnel or chute that compresses the implant for loading into the catheter.

Once the implant is loaded into the catheter, the catheter is then advanced through an artery to the diseased portion of the affected artery using any of the techniques common in the art. Using the catheter the implant is then inserted and positioned within the aneurysm. Once the implant is released from its compressed state, it is allowed to expand within the aneurysm.

When properly located in situ, pursuant to the teachings of this invention, implants or occlusion devices are intended to cause angiographic occlusion of the aneurysm sac. The presence of implants or occlusion devices, optionally including one or more pharmacologic agents borne on each implant, stimulates fibroblast proliferation, growth of scar tissue around the implants and eventual immobilization of the aneurysm.

Advantageously, the implants of the invention can, if desired, comprise reticulated biodurable elastomeric implants having a materials chemistry and microstructure as described herein.

The invention can perhaps be better appreciated from the drawings. In the embodiment of the invention shown in FIGS. 6 to 8, a foam structure 50 comprises two or more sections 52, preferably from about 2 to about 100, that are defined by radiopaque rings, e.g., platinum rings or compression members 54 or similar mechanisms. Foam sections 52 comprise a longitudinally extending flexible mesh 58 defining a lumen 62. A distal spring section 64 attached to the distal end 66 of structure 50 comprises a distal tip 68 and a lumen 70 in communication with lumen 62. At the proximal end 74 of structure 50 a proximal spring 72 is attached to proximal end 74 and has a lumen 76 extending therethrough. A flexible but rigid wire 78 extends through lumen 76, lumen 62, and lumen 70. Wire 78 has a radiopaque tip marker 60. Flexible mesh 58 extends distally as a jacket to cover coil 64 and proximally as a jacket to cover coil 72.

Compressed structure 50 is positioned within a delivery catheter 80 that has a longitudinally extending lumen 82 and a distal radiopaque marker 86. The proximal end 88 of catheter 80 has a narrowed opening 90 that slidably engages a pushing catheter 94.

The proximal end 96 of pushing catheter 94 slidably engages the proximal section 98 of wire 78. The distal end 102 of pushing catheter 94 comprises a radiopaque marker 104 and an opening 106. A flexible loop or wire 108 attached to coil 76 extends through opening 106 to engage wire 78.

To deploy structure 50, as shown in FIG. 7, pusher catheter 94 and wire 78 are advanced distally. As portions of structure 50 extend distally past the distal end 110 of delivery catheter 80, wire 78 is withdrawn in the proximal direction. Eventually, as shown in FIG. 8, wire 78 is withdrawn past opening 106 so that flexible wire 108 releases and structure 50 is free from delivery catheter 80.

Preferably coils 70 and 76 and mesh 58 comprise a biocompatible shape memory alloy or polymer such as nitinol, so that the released structure will assume a non-linear, preferably helical or irregular, shape.

It should be appreciated that in the aspect of the invention shown in FIG. 7 the implant is still connected to the delivery "system" via connecting number 108. This is important because the implant can in this partially delivered condition be maneuvered within the patient to either reposition the implant to optimize placement allowing for a controlled delivery, or even to withdraw or retrieve the implant altogether.

Figure 9:
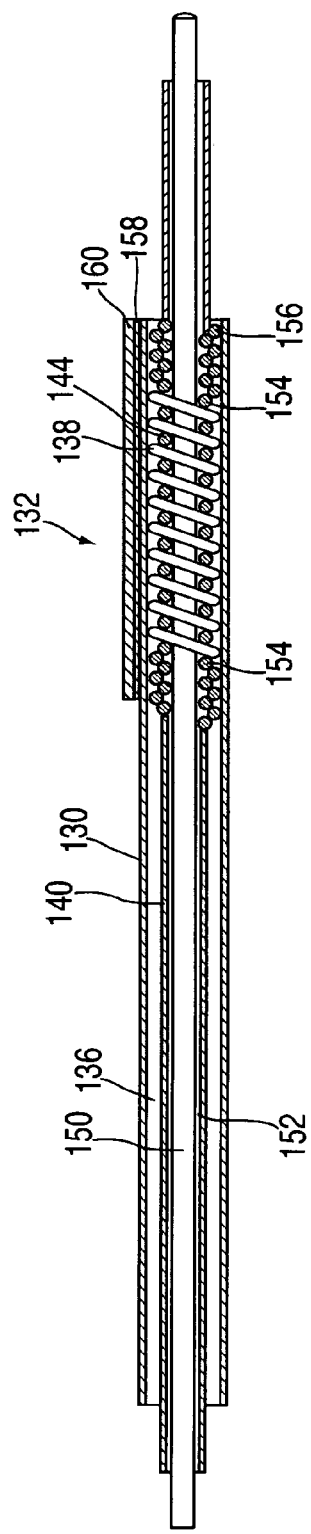
FIGS. 9 and 10 illustrate a further embodiment of the invention where a vascular occlusion device is fixed in position.
Figure 10:
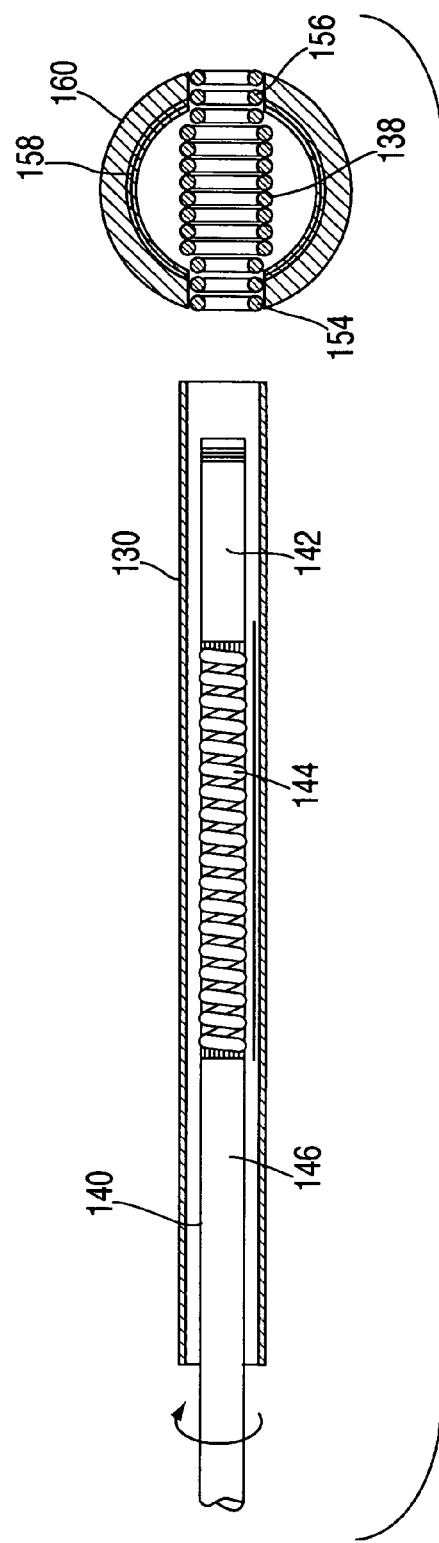

Another embodiment of the invention, a shown in FIGS. 9 and 10, comprises a delivery catheter 130 and a vascular occlusion device 132 positioned at the distal end 134 of catheter 130. Extending within a lumen 136 of catheter 130 and through a lumen formed by a coil 138 in occlusion device 132 is a delivery member 140 that has a distal section 142, a middle section 144, and a proximal section 146. A guidewire 150 extends through lumen 152 formed within delivery member 140.

Coil 138 is wound from one single nitinol wire but it has sections with two different diameters. Coil proximal end 154 and coil distal end 156, which are like two "nuts", each have the same diameter, corresponding to and able to engage the diameter of delivery member middle section 144. The center part of coil 138 has larger a diameter, so that delivery member 140 can move through it freely. To attach occlusion device 132 in a delivery position, it needs to be stretched from a spherical or ball shape into a low profile cylindrical shape by use of a stretching device (not shown). Once device 132 is stretched, it can be locked by inserting delivery member 140 with distal section 142 and engaging proximal nut 154 and distal nut 156 by screw segment 144 to remain in a stretched position for delivery.

For deployment, occlusion device 132 can be released by rotating section 144 proximally catheter 130. As soon as section 144 unscrews from distal nut 156 into the center part of coil 138, the memory force of coil 138 will start compressing back to a sphical or ball shape, as shown in FIG. 10, while section 144 moves proximally from proximal nut 154. Detachment will occur after section 144 unscrews completely from proximal nut 154 of coil 138 and soft distal tip 142 is pulled back into catheter 130. Occlusion device 132 is then released from delivery member 140 at a desired location.

Occlusion device 132 comprises shape memory metallic or polymeric members 158, preferably nitinol, to which a foam layer 160 is attached.

Figure 11:
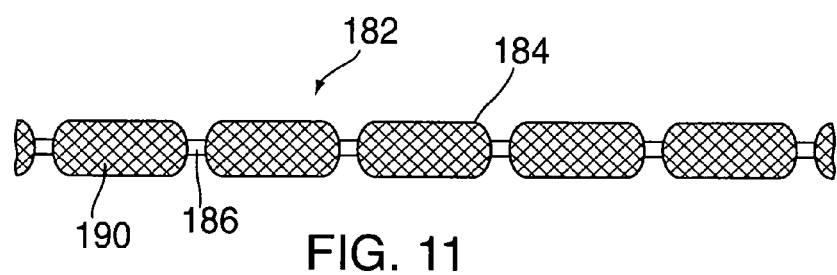

In FIG. 11, an implant 182 is formed from a foam member 184 optionally having a round, square, ellipsoidal, or rectangular cross-section. Radiopaque, preferably platinum, markers 186 are positioned or crimped every about 2 to about 10 mm to form a chain or noodle-like structure. Implant 182 has a reinforcing filament 190 extending through the entire length of implant 182 to prevent implant 182 from breaking or fragmenting, to provide support for pulling and/or pushing during delivery or deployment, and to prevent migration during delivery or deployment. Reinforcing filament 190 can be biosorbable or non-resorbable, preferably non-resorbable, and can be comprised of a polymer such as polyester, a radiopaque metal such as platinum, or a combination thereof, including, but not limited to, known suture materials or suture composites. Moreover, reinforcing filament 190 can be a monofilament, braided rope or wire, or a wire or cable. The length of implant 182 could be from about 5 mm to about 800 mm, preferably from about 50 mm to about 600 mm, and the diameter or effective diameter could be from about 0.25 mm to about 10 mm, preferably from about 0.50 mm to about 2 mm.

Figure 12:
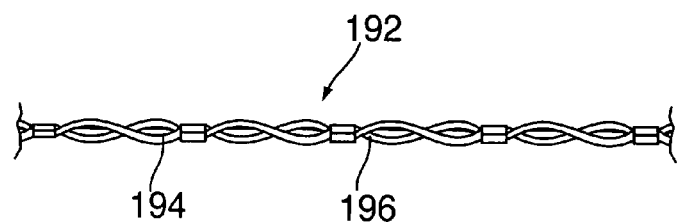

The implant 192 in FIG. 12 comprises two or more, preferably from about 3 to 6, cylindrical or string segments 194 that are held together by a reinforcing filament (not shown) or marker 196 for structural integrity for delivery or deployment or to be blended with other components. As with implant 182, radiopaque markers 196 are crimped from about 2 to about 10 mm apart. The length and effective diameter of implant 192 are approximately the same as those of implant 182.

Figure 13:
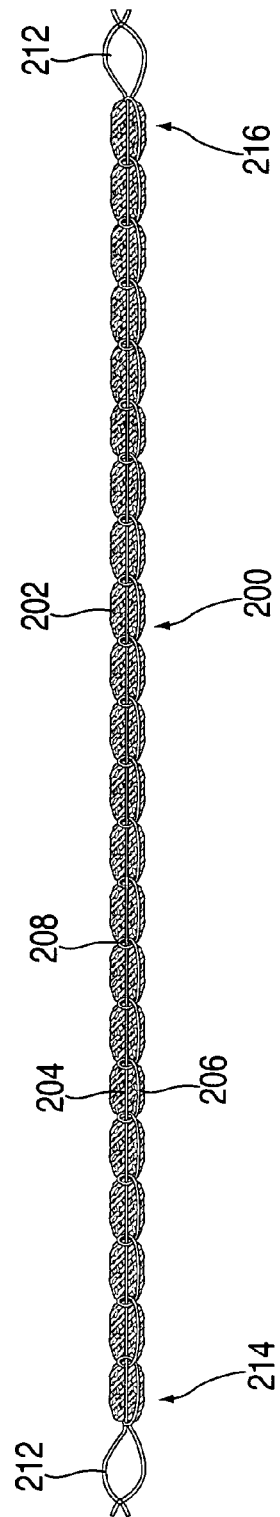
Figure 14:
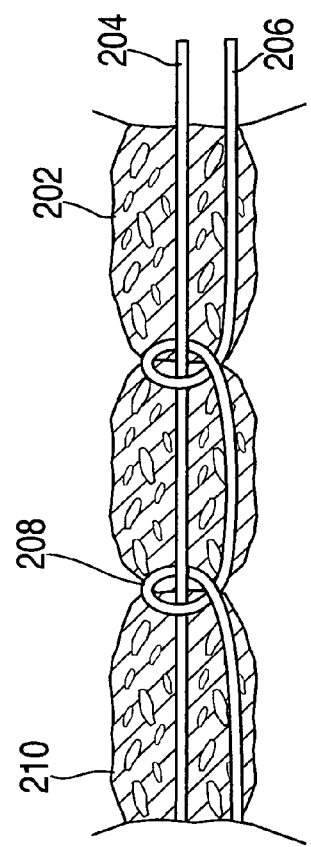

A preferred embodiment of an implant 200, also known as a "Neurostring" or "foam on a string," is shown in FIGS. 13 and 14. Implant 200 is formed from a foam member 202 having a round, square, ellipsoidal or rectangular, but preferably round, cross-section. Two longitudinally extending, essentially parallel reinforcing filaments 204 and 206 extend the length of implant 200, and at regular intervals reinforcing filaments 204 and 206 form knots or ropes 208 that define foam sections 210. The purpose of the knots is to secure the reinforcing filament to the elastomeric matrix. This can be seen more clearly in the detail of FIG. 14. The respective ends of reinforcing filaments 204 and 206 form loops 212 at the proximal and distal ends 214 and 216, respectively, of implant 200.

Reinforcing filaments 204 and 206 can be biosorbable or non-resorbable, preferably non-resorbable, and comprised of a polymer such as polyester, a radiopaque metal such as platinum, or a combination thereof, including, but not limited to, known suture materials or suture composites. Moreover, reinforcing filaments 204 and 206 can each be a monofilament, braided rope or wire, or a wire or cable. The length of implant 200 could be from about 5 mm to about 1500 mm, preferably from about 1 cm to about 50 cm, and the diameter or effective diameter could be from about 0.25 mm to about 12 mm, preferably from about 0.50 mm to about 0.5 mm. The foam sections are each from about 0.5 mm to about 1 cm in length. Each foam section 210 is carefully trimmed or shaved by hand to a desired diameter. The outer diameter of each foam section should be equal to or slightly less than the inner diameter of the corresponding introducer sheath, discussed below. The reinforcing filaments 204 and 206 can be inserted into implant 200 by hand or by mechanical means such as a mechanical stitching or sewing machine.

Figure 15:
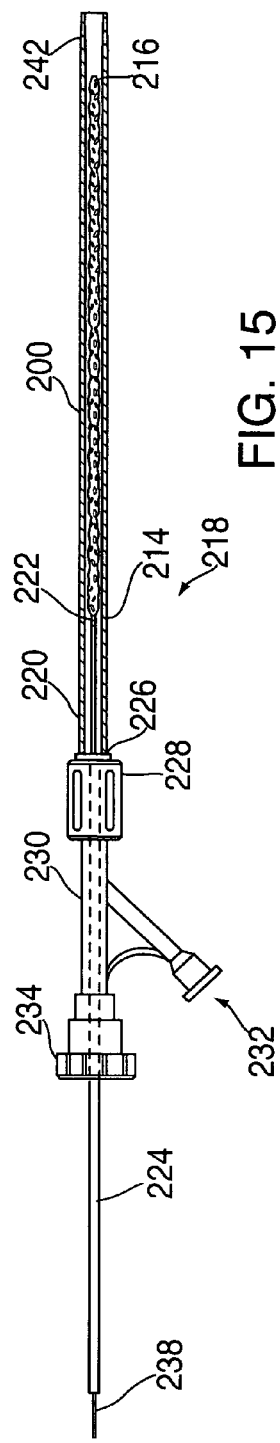

A packaging system 218 for the storage and/or introduction of an implant such as implant 200 or other implants according to the invention is shown in FIG. 15. Proximal end 214 of implant 200 is engaged within an introducer sheath 220 by the distal end 222 of a pusher rod or member 224. The proximal end 226 of sheath 220 engages the distal portion 228 of a manifold or side arm 230, which has an opening 232 for continuous flush. Pusher member 224 extends proximally through valve 234, and pusher member 224 has a lumen (not shown) which receives an interlocking wire 238, which provides support to pusher member 224 and helps retain implant 200.

Figure 16:
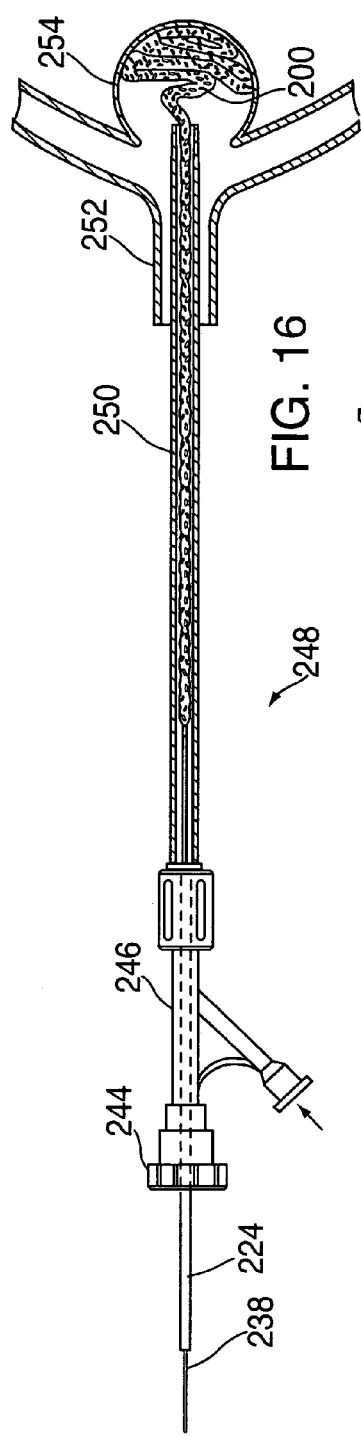

For delivery of implant 200 or another occlusion device according to the invention to a patient, a flushing solution such as saline solution is introduced into opening 232 of system 218 to remove air and straighten out implant 200. Then, the tapered distal tip 242 of sheath 220 is introduced with continuous flushing into the hemostastis valve 244 of a side arm 246 of a micro-catheter assembly 248 such as is shown in FIG. 16. Sheath 220 is inserted into micro-catheter 250, after which sheath 220 and side arm 230 are withdrawn, leaving implant 200, pusher member 224, and interlocking wire 238.

Figure 17:
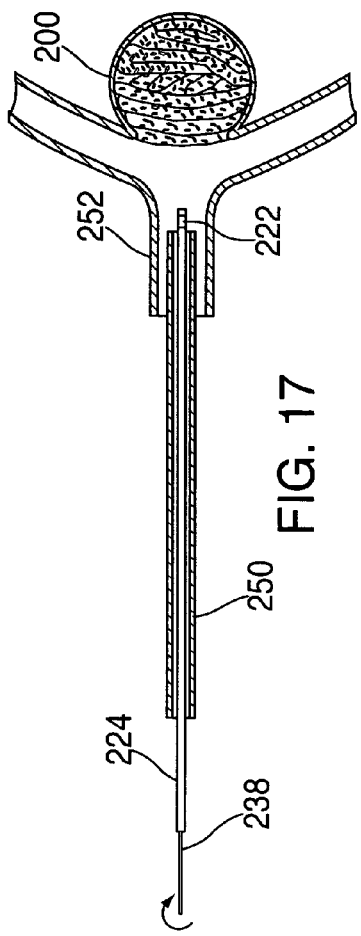

Delivery of implant 200 is shown in FIGS. 16 and 17, where the distal end 216 of implant 200 is advanced through micro-catheter 250 and through an artery 252 to a position adjacent an aneurysm 254. Implant 200 is advanced further to fill aneurysm 254. When aneurysm 254 has been filled, as shown in FIG. 17, the distal end 222 of pusher rod 224 is disengaged from implant 200 and withdrawn through micro-catheter 250.

A detail of the connection between the proximal end 214 of implant 200 and the distal end member 262 of pusher member 224 is shown in FIGS. 18 and 19. Distal end member 262 comprises a lateral opening 264 to receive loop 212 from implant 200 and threading 266. The distal end 268 of wire 238 has reciprocal threads 270 that engage threading 266. In the position shown in FIG. 18, the distal end 268 of wire 238 is adjacent to the internal end surface 274 of distal end 262, to trap loop 212. When wire 238 is rotated to cause wire 238 to disengage from threading 266, loop 212 disengages from wire 238 and pusher member 224 and releases implant 200. Also, preferably distal end member 262 comprises radiopaque material such as platinum to assist an operator during delivery. For example, distal end member 262 could comprise a section of platinum hypotube. More preferably, the distal end 268 of wire 238 is also radiopaque, which assists the operator during the procedure. When distal end 268 and distal end 262 are engaged, there will be a single spot under fluoroscopy; however, when distal end 268 and distal end 262 disengage, and release the loop from the implant, there will then be two separate spots under fluoroscopy to signify that release.

Advancing through the micro-catheter 250 provides controlled delivery or retraction of implant 200 into the aneurysm cavity with the pusher member 224 until desired positioning of implant 200 is accomplished. Due to the nature of the implant material, the implant fills the aneurysm cavity like a liquid complying with the geometry of the cavity. Continuous flush or pump of hydraulically pressurized solution such as saline solution is applied via micro-catheter through the micro-catheter side arm at the proximal end to support or drive the advancement of the implant through the catheter lumen. Dependent upon the size of the aneurysm, single or multiple implants may be necessary to achieve total occlusion. The packing density, that is, the ratio of volume of embolic material to volume of the aneurysm sac, ranges from about 50 to about 200%. Implant 200 can be retracted, before it is detached, and repositioned for precise, controlled deployment and delivery.

Implant 200 is not self-supporting and has no predetermined shape. It conforms significantly better to the geometry of the aneurysm than other implants due to the formation of a light, non-traumatic "string-ball" casting the cavity like a liquid. Because of this important feature the implant material will provide permanent stability of the desired total occlusion. An additional important feature of implant 200 is that it provides excellent tissue ingrowth to seal the aneurysm cavity from the parental artery. There is superior tissue ingrowth due to the porous nature of the reticulated matrix enhanced by structural reticulation created by plication/folding within the aneurysm. Also, plication enhances conformal space filling that eliminates device compaction and recanalization.

Figures 20A, 20B:
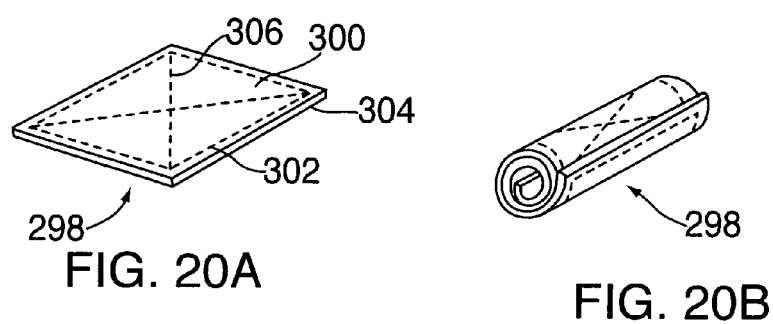

The implant 298 shown in FIGS. 20A and 20B comprises a flat, preferably square or rectangular, member 300 that can be rolled up to fit in a delivery catheter (not shown). Member 300 preferably has surgical sutures, optionally absorbable, or radiopaque wire 302 sewn around the outer edges 304 and also diagonally 306. As shown in FIG. 20B, implant 298 can be rolled up to fit within a lumen of a delivery catheter. Upon deployment implant 298 would unroll to fill an aneurysm sac. An advantage of this particular embodiment is the relatively large surface area that is available for occlusion. It is anticipated that implant 298 could be from about 0.25 mm to about 3 mm in thickness and from about 1 mm to about 50 mm in length on the lateral edges.

Figure 21:
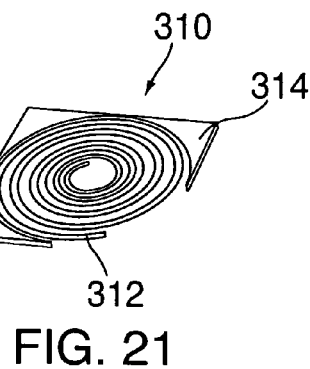

FIG. 21 represents an implant 310 where a thin string structure 312 has been cut from a flat member 314. Structure 312 is similar to implant 182 but with or without the internal suture or wire member. Manufacturing implant 310 in this manner provided memory support without nitinol support.

FIGS. 22A and 22B represent structures that may have an unexpanded shape, for example, cylindrical shape 318, that expands to an expanded shape, for example, spherical shape 320, due to internal frames (not shown). The outer surface 322 of shape 320 could comprise coils or braids, for example, or different shapes can be sutured together using coils and/or patches to provide maximum surface area for occlusion.

Implant 324 shown in FIGS. 23A and 23B is representative of a nitinol or other shape-memory wire member 326 having a foam cover 328. Implant 324 is compressed for delivery, as shown in FIG. 23A, and then expands to the configuration shown in FIG. 23B upon deployment.

A cylindrically-shaped implant 330 with slots 332 is shown in FIGS. 24A and 24B. As can be appreciated in the radial cross-section of FIG. 24B, implant 330 may have one or more radiopaque bend markers 334. An advantage of this shape is that the slots permit the implant to bend to maximize surface area during deployment.

Examples of such shapes include, but are not limited to, spheres, hollow spheres, cylinders, hollow cylinders, noodles, cubes, pyramids, tetrahedrons, hollow cylinders with lateral slots, trapezoids, parallelepipeds, ellipsoids, rods, tubes, or elongated prismatic forms, folded, coiled, helical or other more compact configurations, segmented cylinders where "sausage-like" segments have been formed, flat square or rectangular shapes, daisy shapes, braided shapes, or flat spiral shapes, optionally with surgical suture or radiopaque wire support extending therein.

Certain embodiments of the invention comprise porous, reticulated biodurable elastomeric implants, which are also compressible and exhibit resilience in their recovery, that have a diversity of applications and can be employed, by way of example, in management of vascular malformations, such as for aneurysm control, arteriovenous malfunction, arterial embolization or other vascular abnormalities, or as substrates for pharmaceutically-active agent, e.g., for drug delivery. Thus, as used herein, the term "vascular malformation" includes but is not limited to aneurysms, arteriovenous malfunctions, arterial embolizations and other vascular abnormalities. Other embodiments include reticulated, biodurable elastomeric implants for in vivo delivery via catheter, endoscope, arthroscope, laparoscope, cystoscope, syringe or other suitable delivery-device and can be satisfactorily implanted or otherwise exposed to living tissue and fluids for extended periods of time, for example, at least 29 days.

There is a need in medicine, as recognized by the present invention, for atraumatic implantable devices that can be delivered to an in vivo patient site, for example a site in a human patient, that can occupy that site for extended periods of time without being harmful to the host. In one embodiment, such implantable devices can also eventually become biologically integrated, e.g., ingrown with tissue. Various implants have long been considered potentially useful for local in situ delivery of biologically active agents and more recently have been contemplated as useful for control of endovascular conditions including potentially life-threatening conditions such as cerebral and aortic abdominal aneurysms, arterio venous malfunction, arterial embolization or other vascular abnormalities.

It would be desirable to have an implantable system which, e.g., can optionally cause immediate thrombotic response leading to clot formation, and eventually lead to fibrosis, i.e., allow for and stimulate natural cellular ingrowth and proliferation into vascular malformations and the void space of implantable devices located in vascular malformations, to stabilize and possibly seal off such vascular abnormalities in a biologically sound, effective and lasting manner.

In one embodiment of the invention, cellular entities such as fibroblasts and tissues can invade and grow into a reticulated elastomeric matrix. In due course, such ingrowth can extend into the interior pores and interstices of the inserted reticulated elastomeric matrix. Eventually, the elastomeric matrix can become substantially filled with proliferating cellular ingrowth that provides a mass that can occupy the site or the void spaces in it. The types of tissue ingrowth possible include, but are not limited to, fibrous tissues and endothelial tissues.

In another embodiment of the invention, the implantable device or device system causes cellular ingrowth and proliferation throughout the site, throughout the site boundary, or through some of the exposed surfaces, thereby sealing the site. Over time, this induced fibrovascular entity resulting from tissue ingrowth can cause the implantable device to be incorporated into the aneurysm wall. Tissue ingrowth can lead to very effective resistance to migration of the implantable device over time. It may also prevent recanalization of the aneurysm. In another embodiment, the tissue ingrowth is scar tissue which can be long-lasting, innocuous and/or mechanically stable. In another embodiment, over the course of time, for example, for from 2 weeks to 3 months to 1 year, implanted reticulated elastomeric matrix becomes completely filled and/or encapsulated by tissue, fibrous tissue, scar tissue or the like.

The invention has been described herein with regard to its applicability to aneurysms, particularly cerebral aneurysms. It should be appreciated that the features of the implantable device, its functionality, and interaction with an aneurysm cavity, as indicated above, can be useful in treating a number of arteriovenous malformations ("AVM") or other vascular abnormalities. These include AVMs, anomalies of feeding and draining veins, arteriovenous fistulas, e.g., anomalies of large arteriovenous connections, abdominal aortic aneurysm endograft endoleaks (e.g., inferior mesenteric arteries and lumbar arteries associated with the development of Type II endoleaks in endograft patients).

Shaping and sizing can include custom shaping and sizing to match an implantable device to a specific treatment site in a specific patient, as determined by imaging or other techniques known to those in the art. In particular, one or at least two comprise an implantable device system for treating an undesired cavity, for example, a vascular malformation.

Some materials suitable for fabrication of the implants according to the invention will now be described. Implants useful in this invention or a suitable hydrophobic scaffold comprise a reticulated polymeric matrix formed of a biodurable polymer that is elastomeric and resiliently-compressible so as to regain its shape after being subjected to severe compression during delivery to a biological site such as vascular malformations described here. The structure, morphology and properties of the elastomeric matrices of this invention can be engineered or tailored over a wide range of performance by varying the starting materials and/or the processing conditions for different functional or therapeutic uses.

The inventive implantable device is reticulated, i.e., comprises an interconnected network of pores and channels and voids that provides fluid permeability throughout the implantable device and permits cellular and tissue ingrowth and proliferation into the interior of the implantable device. The inventive implantable device is reticulated, i.e., comprises an interconnected and/or inter-communicating network of pores and channels and voids that provides fluid permeability throughout the implantable device and permits cellular and tissue ingrowth and proliferation into the interior of the implantable device. The inventive implantable device is reticulated, i.e., comprises an interconnected and/or inter-communicating network of pores and/or voids and/or channels that provides fluid permeability throughout the implantable device and permits cellular and tissue ingrowth and proliferation into the interior of the implantable device. The biodurable elastomeric matrix or material is considered to be reticulated because its microstructure or the interior structure comprises inter-connected and inter-communicating pores and/or voids bounded by configuration of the struts and intersections that constitute the solid structure. The continuous interconnected void phase is the principle feature of a reticulated structure.

Preferred scaffold materials for the implants have a reticulated structure with sufficient and required liquid permeability and thus selected to permit blood, or other appropriate bodily fluid, and cells and tissues to access interior surfaces of the implants. This happens due to the presence of inter-connected and inter-communicating, reticulated open pores and/or voids and/or channels that form fluid passageways or fluid permeability providing fluid access all through.

Preferred materials are at least partially hydrophobic reticulated, elastomeric polymeric matrix for fabricating implants according to the invention are flexible and resilient in recovery, so that the implants are also compressible materials enabling the implants to be compressed and, once the compressive force is released, to then recover to, or toward, substantially their original size and shape. For example, an implant can be compressed from a relaxed configuration or a size and shape to a compressed size and shape under ambient conditions, e.g., at 25° C. to fit into the introducer instrument for insertion into the vascular malformations (such as an aneurysm sac or endoloeak nexus within the sac). Alternatively, an implant may be supplied to the medical practitioner performing the implantation operation, in a compressed configuration, for example, contained in a package, preferably a sterile package. The resiliency of the elastomeric matrix that is used to fabricate the implant causes it to recover to a working size and configuration in situ, at the implantation site, after being released from its compressed state within the introducer instrument. The working size and shape or configuration can be substantially similar to original size and shape after the in situ recovery.

Preferred scaffolds are reticulated elastomeric polymeric materials having sufficient structural integrity and durability to endure the intended biological environment, for the intended period of implantation. For structure and durability, at least partially hydrophobic polymeric scaffold materials are preferred although other materials may be employed if they meet the requirements described herein. Useful materials are preferably elastomeric in that they can be compressed and can resiliently recover to substantially the pre-compression state. Alternative reticulated polymeric materials with interconnected pores or networks of pores that permit biological fluids to have ready access throughout the interior of an implant may be employed, for example, woven or non-woven fabrics or networked composites of microstructural elements of various forms.

A partially hydrophobic scaffold is preferably constructed of a material selected to be sufficiently biodurable, for the intended period of implantation that the implant will not lose its structural integrity during the implantation time in a biological environment. The biodurable elastomeric matrices forming the scaffold do not exhibit significant symptoms of breakdown, degradation, erosion or significant deterioration of mechanical properties relevant to their use when exposed to biological environments and/or bodily stresses for periods of time commensurate with the use of the implantable device. In one embodiment, the desired period of exposure is to be understood to be at least 29 days, preferably several weeks and most preferably 2 to 5 years or more. This measure is intended to avoid scaffold materials that may decompose or degrade into fragments, for example, fragments that could have undesirable effects such as causing an unwanted tissue response.

The void phase, preferably continuous and interconnected, of the reticulated polymeric matrix that is used to fabricate the implant of this invention may comprise as little as 50% by volume of the elastomeric matrix, referring to the volume provided by the interstitial spaces of elastomeric matrix before any optional interior pore surface coating or layering is applied. In one embodiment, the volume of void phase as just defined, is from about 70% to about 99% of the volume of elastomeric matrix. In another embodiment, the volume of void phase is from about 80% to about 98% of the volume of elastomeric matrix. In another embodiment, the volume of void phase is from about 90% to about 98% of the volume of elastomeric matrix.

As used herein, when a pore is spherical or substantially spherical, its largest transverse dimension is equivalent to the diameter of the pore. When a pore is non-spherical, for example, ellipsoidal or tetrahedral, its largest transverse dimension is equivalent to the greatest distance within the pore from one pore surface to another, e.g., the major axis length for an ellipsoidal pore or the length of the longest side for a tetrahedral pore. For those skilled in the art, one can routinely estimate the pore frequency from the average cell diameter in microns.

In one embodiment relating to vascular malformation applications and the like, to encourage cellular ingrowth and proliferation and to provide adequate fluid permeability, the average diameter or other largest transverse dimension of pores is at least about 50 µm. In another embodiment, the average diameter or other largest transverse dimension of pores is at least about 100 µm. In another embodiment, the average diameter or other largest transverse dimension of pores is at least about 150 µm. In another embodiment, the average diameter or other largest transverse dimension of pores is at least about 250 µm. In another embodiment, the average diameter or other largest transverse dimension of pores is greater than about 250 µm. In another embodiment, the average diameter or other largest transverse dimension of pores is greater than 250 µm. In another embodiment, the average diameter or other largest transverse dimension of pores is at least about 275 µm. In another embodiment, the average diameter or other largest transverse dimension of pores is greater than about 275 µm. In another embodiment, the average diameter or other largest transverse dimension of pores is greater than 275 µm. In another embodiment, the average diameter or other largest transverse dimension of pores is at least about 300 µm. In another embodiment, the average diameter or other largest transverse dimension of pores is greater than about 300 µm. In another embodiment, the average diameter or other largest transverse dimension of pores is greater than 300 µm.

In another embodiment relating to vascular malformation applications and the like, the average diameter or other largest transverse dimension of pores is not greater than about 900 µm. In another embodiment, the average diameter or other largest transverse dimension of pores is not greater than about 850 µm. In another embodiment, the average diameter or other largest transverse dimension of pores is not greater than about 800 µm. In another embodiment, the average diameter or other largest transverse dimension of pores is not greater than about 700 µm. In another embodiment, the average diameter or other largest transverse dimension of pores is not greater than about 600 µm. In another embodiment, the average diameter or other largest transverse dimension of pores is not greater than about 500 µm.

In one embodiment, the reticulated polymeric matrix that is used to fabricate the implants of this invention has any suitable bulk density, also known as specific gravity, consistent with its other properties. For example, in one embodiment, the bulk density may be from about 0.005 to about 0.15 g/cc (from about 0.31 to about 9.4 lb/ft$^3$), preferably from about 0.015 to about 0.115 g/cc (from about 0.93 to about 7.2 lb/ft$^3$) and most preferably from about 0.024 to about 0.104 g/cc (from about 1.5 to about 6.5 lb/ft$^3$).

The reticulated elastomeric matrix has sufficient tensile strength such that it can withstand normal manual or mechanical handling during its intended application and during post-processing steps that may be required or desired without tearing, breaking, crumbling, fragmenting or otherwise disintegrating, shedding pieces or particles, or otherwise losing its structural integrity. The tensile strength of the starting material(s) should not be so high as to interfere with the fabrication or other processing of elastomeric matrix. Thus, for example, in one embodiment, the reticulated polymeric matrix that is used to fabricate the implants of this invention may have a tensile strength of from about 700 to about 52,500 kg/m$^2$ (from about 1 to about 75 psi). In another embodiment, elastomeric matrix may have a tensile strength of from about 7000 to about 28,000 kg/m$^2$ (from about 10 to about 40 psi). Sufficient ultimate tensile elongation is also desirable. For example, in another embodiment, reticulated elastomeric matrix has an ultimate tensile elongation of at least about 50% to at least about 500%. In yet another embodiment, reticulated elastomeric matrix has an ultimate tensile elongation of at least 75% to at least about 300%.

One embodiment for use in the practice of the invention is a reticulated elastomeric implant which is sufficiently flexible and resilient, i.e., resiliently-compressible, to enable it to be initially compressed under ambient conditions, e.g., at 25° C., from a relaxed configuration to a first, compact configuration for delivery via a delivery-device, e.g., catheter, endoscope, syringe, cystoscope, trocar or other suitable introducer instrument, for delivery in vitro and, thereafter, to expand to a second, working configuration in situ. Furthermore, in another embodiment, an elastomeric matrix has the herein described resilient-compressibility after being compressed about 5-95% of an original dimension (e.g., compressed about $^{19}/_{20}$th-$^{1}/_{20}$th of an original dimension). In another embodiment, an elastomeric matrix has the herein described resilient-compressibility after being compressed about 10-90% of an original dimension (e.g., compressed about $^{9}/_{10}$th-$^{1}/_{10}$th of an original dimension). As used herein, elastomeric implant has "resilient-compressibility", i.e., is "resiliently-compressible", when the second, working configuration, in vitro, is at least about 50% of the size of the relaxed configuration in at least one dimension. In another embodiment, the resilient-compressibility of elastomeric implant is such that the second, working configuration, in vitro, is at least about 80% of the size of the relaxed configuration in at least one dimension. In another embodiment, the resilient-compressibility of elastomeric implant is such that the second, working configuration, in vitro, is at least about 90% of the size of the relaxed configuration in at least one dimension. In another embodiment, the resilient-compressibility of elastomeric implant is such that the second, working configuration, in vitro, is at least about 97% of the size of the relaxed configuration in at least one dimension.

In another embodiment, an elastomeric matrix has the herein described resilient-compressibility after being compressed about 5-95% of its original volume (e.g., compressed about $^{19}/_{20}$th-$^{1}/_{20}$th of its original volume). In another embodiment, an elastomeric matrix has the herein described resilient-compressibility after being compressed about 10-90% of its original volume (e.g., compressed about $^{9}/_{10}$th-$^{1}/_{10}$th of its original volume). As used herein, "volume" is the volume swept-out by the outermost three-dimensional contour of the elastomeric matrix. In another embodiment, the resilient-compressibility of elastomeric implant is such that the second, working configuration, in vivo, is at least about 50% of the volume occupied by the relaxed configuration. In another embodiment, the resilient-compressibility of elastomeric implant is such that the second, working configuration, in vivo, is at least about 80% of the volume occupied by the relaxed configuration. In another embodiment, the resilient-compressibility of elastomeric implant is such that the second, working configuration, in vivo, is at least about 90% of the volume occupied by the relaxed configuration. In another embodiment, the resilient-compressibility of elastomeric implant is such that the second, working configuration, in vivo, occupies at least about 97% of the of volume occupied by the elastomeric matrix in its relaxed configuration.

Without being bound by any particular theory, it is believed that the absence or substantial absence of cell walls in reticulated implants when compressed to very high degree will allow them to demonstrate resilient recovery in shorter time (such as recovery time of under 15 seconds when compressed to 75% of their relaxed configuration for 10 minutes and recovery time of under 35 seconds when compressed to 90% of their relaxed configuration for 10 minutes) as compared to un-reticulated porous foams.

In one embodiment, reticulated elastomeric matrix that is used to fabricate the implants of this invention has a compressive strength of from about 700 to about 70,000 kg/m$^2$ (from about 1 to about 100 psi) at 50% compression strain. In another embodiment, reticulated elastomeric matrix has a compressive strength of from about 1,400 to about 105,000 kg/M$^2$ (from about 2 to about 150 psi) at 75% compression strain.

In another embodiment, reticulated elastomeric matrix that is used to fabricate the implants of this invention has a compression set, when compressed to 50% of its thickness at about 25° C., of not more than about 30%. In another embodiment, elastomeric matrix has a compression set of not more than about 20%. In another embodiment, elastomeric matrix has a compression set of not more than about 10%. In another embodiment, elastomeric matrix has a compression set of not more than about 5%.

In another embodiment, reticulated elastomeric matrix that is used to fabricate the implants of this invention has a tear strength, of from about 0.18 to about 1.78 kg/linear cm (from about 1 to about 10 lbs/linear inch).

In another embodiment of the invention the reticulated elastomeric matrix that is used to fabricate the implant can be readily permeable to liquids, permitting flow of liquids, including blood, through the composite device of the invention. The water permeability of the reticulated elastomeric matrix is from about 50 l/min./psi/cm$^2$ to about 500 l/min./psi/cm$^2$, preferably from about 100 l/min./psi/cm$^2$ to about 300 l/min./psi/cm$^2$. In contrast, permeability of the unreticulated elastomeric matrix is below about 1 l/min./psi/cm$^2$. In another embodiment, the permeability of the unreticulated elastomeric amtrix is below about 5 l/min./psi/cm$^2$.

In general, suitable biodurable reticulated elastomeric partially hydrophobic polymeric matrix that is used to fabricate the implant of this invention or for use as scaffold material for the implant in the practice of the present invention, in one embodiment sufficiently well characterized, comprise elastomers that have or can be formulated with the desirable mechanical properties described in the present specification and have a chemistry favorable to biodurability such that they provide a reasonable expectation of adequate biodurability.

Various biodurable reticulated hydrophobic polyurethane materials are suitable for this purpose. In one embodiment, structural materials for the inventive reticulated elastomers are synthetic polymers, especially, but not exclusively, elastomeric polymers that are resistant to biological degradation, for example, polycarbonate polyurethane-urea, polycarbonate polyurea-urethane, polycarbonate polyurethane, polycarbonate polysiloxane polyurethane, and polysiloxane polyurethane, and the like. Such elastomers are generally hydrophobic but, pursuant to the invention, may be treated to have surfaces that are less hydrophobic or somewhat hydrophilic. In another embodiment, such elastomers may be produced with surfaces that are less hydrophobic or somewhat hydrophilic.

The invention can employ, for implanting, a biodurable reticulatable elastomeric partially hydrophobic polymeric scaffold material or matrix for fabricating the implant or a material. More particularly, in one embodiment, the invention provides a biodurable elastomeric polyurethane scaffold material or matrix which is made by synthesizing the scaffold material or matrix preferably from a polycarbonate polyol component and an isocyanate component by polymerization, cross-linking and foaming, thereby forming pores, followed by reticulation of the porous material to provide a biodurable reticulated elastomeric product with inter-connected and/or inter-communicating pores and channels. The product is designated as a polycarbonate polyurethane, being a polymer comprising urethane groups formed from, e.g., the hydroxyl groups of the polycarbonate polyol component and the isocyanate groups of the isocyanate component. In another embodiment, the invention provides a biodurable elastomeric polyurethane scaffold material or matrix which is made by synthesizing the scaffold material or matrix preferably from a polycarbonate polyol component and an isocyanate component by polymerization, cross-linking and foaming, thereby forming pores, and using water as a blowing agent and/or foaming agent during the synthesis, followed by reticulation of the porous material to provide a biodurable reticulated elastomeric product with inter-connected and/or inter-communicating pores and channels. This product is designated as a polycarbonate polyurethane-urea or polycarbonate poly-urea-urethane, being a polymer comprising urethane groups formed from, e.g., the hydroxyl groups of the polycarbonate polyol component and the isocyanate groups of the isocyanate component and also comprising urea groups formed from reaction of water with the isocyanate groups. In all of these embodiments, the process employs controlled chemistry to provide a reticulated elastomeric matrix or product with good biodurability characteristics. The matrix or product employing chemistry that avoids biologically undesirable or nocuous constituents therein.

In one embodiment, the starting material for synthesizing the biodurable reticulated elastomeric partially hydrophobic polymeric matrix contains at least one polyol component to provide the so-called soft segement. For the purposes of this application, the term "polyol component" includes molecules comprising, on the average, about 2 hydroxyl groups per molecule, i.e., a difunctional polyol or a diol, as well as those molecules comprising, on the average, greater than about 2 hydroxyl groups per molecule, i.e., a polyol or a multi-functional polyol. In one embodiment, this soft segment polyol is terminated with hydroxyl groups, either primary or secondary. Exemplary polyols can comprise, on the average, from about 2 to about 5 hydroxyl groups per molecule. In one embodiment, as one starting material, the process employs a difunctional polyol component in which the hydroxyl group functionality of the diol is about 2. In another embodiment, the soft segment is composed of a polyol component that is generally of a relatively low molecular weight, typically from about 500 to about 6,000 daltons and preferably between 1000 to 2500 daltons. Examples of suitable polyol components include but not limited to polycarbonate polyol, hydrocarbon polyol, polysiloxane polyol, poly(carbonate-co-hydrocarbon) polyol, poly(carbonate-co-siloxane) polyol, poly(hydrocarbon-co-siloxane) polyol, polysiloxane polyol and copolymers and mixtures thereof.

In one embodiment, the starting material for synthesizing the biodurable reticulated elastomeric partially hydrophobic polymeric matrix contains at least one isocyanate component and, optionally, at least one chain extender component to provide the so-called "hard segment". In one embodiment, the starting material for synthesizing the biodurable reticulated elastomeric partially hydrophobic polymeric matrix contains at least one isocyanate component. For the purposes of this application, the term "isocyanate component" includes molecules comprising, on the average, about 2 isocyanate groups per molecule as well as those molecules comprising, on the average, greater than about 2 isocyanate groups per molecule. The isocyanate groups of the isocyanate component are reactive with reactive hydrogen groups of the other ingredients, e.g., with hydrogen bonded to oxygen in hydroxyl groups and with hydrogen bonded to nitrogen in amine groups of the polyol component, chain extender, crosslinker and/or water. In one embodiment, the average number of isocyanate groups per molecule in the isocyanate component is about 2. In another embodiment, the average number of isocyanate groups per molecule in the isocyanate component is greater than about 2 is greater than 2.

In one embodiment, a small quantity of an optional ingredient, such as a multi-functional hydroxyl compound or other cross-linker having a functionality greater than 2, is present to allow crosslinking and/or to achieve a stable foam, i.e., a foam that does not collapse to become non-foamlike. Alternatively, or in addition, polyfunctional adducts of aliphatic and cycloaliphatic isocyanates can be used to impart cross-linking in combination with aromatic diisocyanates. Alternatively, or in addition, polyfunctional adducts of aliphatic and cycloaliphatic isocyanates can be used to impart cross-linking in combination with aliphatic diisocyanates. The presence of these components and adducts with functionality higher than 2 in the hard segment component allows for cross-linking to occur.

Exemplary diisocyanates include aliphatic diisocyanates, isocyanates comprising aromatic groups, the so-called "aromatic diisocyanates", and mixtures thereof. Aliphatic diisocyanates include tetramethylene diisocyanate, cyclohexane-1,2-diisocyanate, cyclohexane-1,4-diisocyanate, hexamethylene diisocyanate, isophorone diisocyanate, methylene-bis-(p-cyclohexyl isocyanate) ("H12 MDI"), and mixtures thereof. Aromatic diisocyanates include p-phenylene diisocyanate, 4,4'-diphenylmethane diisocyanate ("4,4'-MDI"), 2,4'-diphenylmethane diisocyanate ("2,4'-MDI"), polymeric MDI, and mixtures thereof. Examples of optional chain extenders include diols, diamines, alkanol amines or a mixture thereof.

In one embodiment, the starting material for synthesizing the biodurable reticulated elastomeric partially hydrophobic polymeric matrix contains at least one blowing agent such as water. Other exemplary blowing agents include the physical blowing agents, e.g., volatile organic chemicals such as hydrocarbons, ethanol and acetone, and various fluorocarbons, hydrofluorocarbons, chlorofluorocarbons, and hydrochlorofluorocarbons. In one embodiment, the hard segments also contain a urea component formed during foaming reaction with water. In one embodiment, the reaction of water with an isocyanate group yields carbon dioxide, which serves as a blowing agent. The amount of blowing agent, e.g., water, is adjusted to obtain different densities of non-reticulated foams. A reduced amount of blowing agent such as water may reduce the number of urea linkages in the material.

In one embodiment, implantable device can be rendered radiopaque to facilitate in vivo imaging, for example, by adhering to, covalently bonding to and/or incorporating into the elastomeric matrix itself particles of a radio-opaque material. Radio-opaque materials include titanium, tantalum, tungsten, barium sulfate or other suitable material known to those skilled in the art.

In one embodiment, the starting material of the biodurable reticulated elastomeric partially hydrophobic polymeric matrix is a commercial polyurethane polymers are linear, not crosslinked, polymers, therefore, they are soluble, can be melted, readily analyzable and readily characterizable. In this embodiment, the starting polymer provides good biodurability characteristics. The reticulated elastomeric matrix is produced by taking a solution of the commercial polymer such as polyurethane and charging it into a mold that has been fabricated with surfaces defining a microstructural configuration for the final implant or scaffold, solidifying the polymeric material and removing the sacrificial mold by melting, dissolving or subliming-away the sacrificial mold. The matrix or product employing a foaming process that avoids biologically undesirable or nocuous constituents therein.

Of particular interest are thermoplastic elastomers such as polyurethanes whose chemistry is associated with good biodurability properties, for example. In one embodiment, such thermoplastic polyurethane elastomers include polycarbonate polyurethanes, polysiloxane polyurethanes, polyurethanes with so-called "mixed" soft segments, and mixtures thereof. Mixed soft segment polyurethanes are known to those skilled in the art and include, e.g., polycarbonate-polysiloxane polyurethanes. In another embodiment, the thermoplastic polyurethane elastomer comprises at least one diisocyanate in the isocyanate component, at least one chain extender and at least one diol, and may be formed from any combination of the diisocyanates, difunctional chain extenders and diols described in detail above. Some suitable thermoplastic polyurethanes for practicing the invention, in one embodiment suitably characterized as described herein, include: polyurethanes with mixed soft segments comprising polysiloxane together with a polycarbonate component.

In one embodiment, the weight average molecular weight of the thermoplastic elastomer is from about 30,000 to about 500,000 Daltons. In another embodiment, the weight average molecular weight of the thermoplastic elastomer is from about 50,000 to about 250,000 Daltons.

Some commercially-available thermoplastic elastomers suitable for use in practicing the present invention include the line of polycarbonate polyurethanes supplied under the trademark BIONATE® by The Polymer Technology Group Inc. (Berkeley, Calif.). For example, the very well-characterized grades of polycarbonate polyurethane polymer BIONATE® 80A, 55 and 90 are soluble in THF, DMF, DMAT, DMSO, or a mixture of two or more thereof, processable, reportedly have good mechanical properties, lack cytotoxicity, lack mutagenicity, lack carcinogenicity and are non-hemolytic. Another commercially-available elastomer suitable for use in practicing the present invention is the CHRONOFLEX® C line of biodurable medical grade polycarbonate aromatic polyurethane thermoplastic elastomers available from CardioTech International, Inc. (Woburn, Mass.).

Other possible embodiments of the materials used to fabricate the implants of this invention are described in co-pending, commonly assigned U.S. patent applications Ser. No. 10/749,742, filed Dec. 30, 2003, titled "Reticulated Elastomeric Matrices, Their Manufacture and Use in Implantable Devices", Ser. No. 10/848,624, filed May 17, 2004, titled "Reticulated Elastomeric Matrices, Their Manufacture and Use In Implantable Devices", and Ser. No. 10/990,982, filed Jul. 27, 2004, titled "Endovascular Treatment Devices and Methods", each of which is incorporated herein by reference in its entirely.

If desired, the reticulated elastomeric implants or implants for packing the aneurysm sac or for other vascular occlusion can be rendered radiopaque to allow for visualization of the implants in situ by the clinician during and after the procedure, employing radioimaging. Any suitable radiopaque agent that can be covalently bound, adhered or otherwise attached to the reticulated polymeric implants may be employed including without limitation, tantalum and barium sulfate. In addition to incorporating radiopaque agents such as tantalum into the implant material itself, a further embodiment of the invention encompasses the use of radiopaque metallic components to impart radiopacity to the implant. For example, thin filaments comprised of metals with shape memory properties such as platinum or nitinol can be embedded into the implant and may be in the form of a straight or curved wire, helical or coil-like structure, umbrella structure, or other structure generally known to those skilled in the art. Alternatively, a metallic frame around the implant may also be used to impart radiopacity. The metallic frame may be in the form of a tubular structure similar to a stent, a helical or coil-like structure, an umbrella structure, or other structure generally known to those skilled in the art. Attachment of radiopaque metallic components to the implant can be accomplished by means including but not limited to chemical bonding or adhesion, suturing, pressure fitting, compression fitting, and other physical methods.

Some optional embodiments of the invention comprise apparatus or devices and treatment methods employing biodurable reticulated elastomeric implants 36 into which biologically active agents are incorporated for the matrix to be used for controlled release of pharmaceutically-active agents, such as a drug, and for other medical applications. Any suitable agents may be employed as will be apparent to those skilled in the art, including, for example, but without limitation thrombogenic agents, e.g., thrombin, anti-inflammatory agents, and other therapeutic agents that may be used for the treatment of abdominal aortic aneurysms. The invention includes embodiments wherein the reticulated elastomeric material of the implants is employed as a drug delivery platform for localized administration of biologically active agents into the aneurysm sac. Such materials may optionally be secured to the interior surfaces of elastomeric matrix directly or through a coating. In one embodiment of the invention the controllable characteristics of the implants are selected to promote a constant rate of drug release during the intended period of implantation.

The implants with reticulated structure with sufficient and required liquid permeability and permit blood, or other appropriate bodily fluid, to access interior surfaces of the implants, which optionally are drug-bearing. This happens due to the presence of inter-connected, reticulated open pores that form fluid passageways or fluid permeability providing fluid access all through and to the interior of the matrix for elution of pharmaceutically-active agents, e.g., a drug, or other biologically useful materials.

In a further embodiment of the invention, the pores of biodurable reticulated elastomeric matrix that are used to fabricate the implants of this invention are coated or filled with a cellular ingrowth promoter. In another embodiment, the promoter can be foamed. In another embodiment, the promoter can be present as a film. The promoter can be a biodegradable material to promote cellular invasion of pores biodurable reticulated elastomeric matrix that are used to fabricate the implants of this invention in vivo. Promoters include naturally occurring materials that can be enzymatically degraded in the human body or are hydrolytically unstable in the human body, such as fibrin, fibrinogen collagen, elastin, hyajuronic acid and absorbable biocompatible polysaccharides, such as chitosan, starch, fatty acids (and esters thereof), glucoso-glycans and hyaluronic acid. In some embodiments, the pore surface of the biodurable reticulated elastomeric matrix that are used to fabricate the implants of this invention is coated or impregnated, as described in the previous section but substituting the promoter for the biocompatible polymer or adding the promoter to the biocompatible polymer, to encourage cellular ingrowth and proliferation.

One possible material for use in the present invention comprises a resiliently compressible composite polyurethane material comprising a hydrophilic foam coated on and throughout the pore surfaces of a hydrophobic foam scaffold. One suitable such material is the composite foam disclosed in co-pending, commonly assigned U.S. patent applications Ser. No. 10/692,055, filed Oct. 22, 2003, Ser. No. 10/749,742, filed Dec. 30, 2003, Ser. No. 10/848,624, filed May 17, 2004, and Ser. No. 10/900,982, filed Jul. 27, 2004, each of which is incorporated herein by reference in its entirety. The hydrophobic foam provides support and resilient compressibility enabling the desired collapsing of the implant for delivery and reconstitution in situ.

The reticulated biodurable elastomeric and at least partially hydrophilic material can be used to carry a variety of therapeutically useful agents, for example, agents that can aid in the healing of the aneurysm, such as elastin, collagen or other growth factors that will foster fibroblast proliferation and ingrowth into the aneurysm, agents to render the foam implant non-thrombogenic, or inflammatory chemicals to foster scarring of the aneurysm. Furthermore the hydrophilic foam, or other agent immobilizing means, can be used to carry genetic therapies, e.g. for replacement of missing enzymes, to treat atherosclerotic plaques at a local level, and to release agents such as antioxidants to help combat known risk factors of aneurysm.

Pursuant to the present invention it is contemplated that the pore surfaces may employ other means besides a hydrophilic foam to secure desired treatment agents to the hydrophobic foam scaffold.

The agents contained within the implant can provide an inflammatory response within the aneurysm, causing the walls of the aneurysm to scar and thicken. This can be accomplished using any suitable inflammation inducing chemicals, such as sclerosants like sodium tetradecyl sulphate (STS), polyiodinated iodine, hypertonic saline or other hypertonic salt solution. Additionally, the implant can contain factors that will induce fibroblast proliferation, such as growth factors, tumor necrosis factor and cytokines.

EXAMPLES

Example 1

Fabrication of a Crosslinked Reticulated Polyurethane Matrix

The aromatic isocyanate RUBINATE 9258 (from Huntsman) was used as the isocyanate component. RUBINATE 9258, which is a liquid at 25° C., contains 4,4'-MDI and 2,4'-MDI and has an isocyanate functionality of about 2.33. A diol, poly(1,6-hexanecarbonate)diol (POLY-CD CD220 from Arch Chemicals) with a molecular weight of about 2,000 Daltons was used as the polyol component and was a solid at 25° C. Distilled water was used as the blowing agent. The blowing catalyst used was the tertiary amine triethylenediamine (33% in dipropylene glycol; DABCO 33LV from Air Products). A silicone-based surfactant was

TABLE 1

| Ingredient used (TEGOSTAB ® BF 2370 from Goldschmidt). A cell-opener was used (ORTEGOL ® 501 from Goldschmidt). The viscosity modifier propylene carbonate (from Sigma-Aldrich) was present to reduce the viscosity. The proportions of the components that were used are set forth in the following table: | Parts by Weight |
|---|---|
| Polyol Component | 100 |
| Viscosity Modifier | 5.80 |
| Surfactant | 0.66 |
| Cell Opener | 1.00 |
| Isocyanate Component | 47.25 |
| Isocyanate Index | 1.00 |
| Distilled Water | 2.38 |
| Blowing Catalyst | 0.53 |

The polyol component was liquefied at 70° C. in a circulating-air oven, and 100 g thereof was weighed out into a polyethylene cup. 5.8 g of viscosity modifier was added to the polyol component to reduce the viscosity, and the ingredients were mixed at 3100 rpm for 15 seconds with the mixing shaft of a drill mixer to form "Mix-1". 0.66 g of surfactant was added to Mix-1, and the ingredients were mixed as described above for 15 seconds to form "Mix-2". Thereafter, 1.00 g of cell opener was added to Mix-2, and the ingredients were mixed as described above for 15 seconds to form "Mix-3". 47.25 g of isocyanate component were added to Mix-3, and the ingredients were mixed for 60±10 seconds to form "System A".

2.38 g of distilled water was mixed with 0.53 g of blowing catalyst in a small plastic cup for 60 seconds with a glass rod to form "System B".

System B was poured into System A as quickly as possible while avoiding spillage. The ingredients were mixed vigorously with the drill mixer as described above for 10 seconds and then poured into a 22.9 cm×20.3 cm×12.7 cm (9 in.×8 in.×5 in.) cardboard box with its inside surfaces covered by aluminum foil. The foaming profile was as follows: 10 seconds mixing time, 17 seconds cream time, and 85 seconds rise time.

Two minutes after the beginning of foaming, i.e., the time when Systems A and B were combined, the foam was placed into a circulating-air oven maintained at 100-105° C. for curing for from about 55 to about 60 minutes. Then, the foam was removed from the oven and cooled for 15 minutes at about 25° C. The skin was removed from each side using a band saw. Thereafter, hand pressure was applied to each side of the foam to open the cell windows. The foam was replaced into the circulating-air oven and postcured at 100-105° C. for an additional four hours.

The average pore diameter of the foam, as determined from optical microscopy observations, was greater than about 275 µm.

The following foam testing was carried out according to ASTM D3574: Bulk density was measured using specimens of dimensions 50 mm×50 mm×25 mm. The density was calculated by dividing the weight of the sample by the volume of the specimen. A density value of 2.81 lbs/ft$^3$ (0.0450 g/cc) was obtained.

Tensile tests were conducted on samples that were cut either parallel to or perpendicular to the direction of foam rise. The dog-bone shaped tensile specimens were cut from blocks of foam. Each test specimen measured about 12.5 mm thick, about 25.4 mm wide, and about 140 mm long; the gage length of each specimen was 35 mm and the gage width of each specimen was 6.5 mm. Tensile properties (tensile strength and elongation at break) were measured using an INSTRON Universal Testing Instrument Model 1122 with a cross-head speed of 500 mm/min (19.6 inches/minute). The average tensile strength perpendicular to the direction of foam rise was determined as 29.3 psi (20,630 kg/M²). The elongation to break perpendicular to the direction of foam rise was determined to be 266%.

The measurement of the liquid flow through the material is measured in the following way using a liquid permeability apparatus or Liquid Permeaeter (Porous Materials, Inc., Ithaca, N.Y.). The foam sample was 8.5 mm in thickness and covered a hole 6.6 mm in diameter in the center of a metal plate that was placed at the bottom of the Liquid Permeaeter filled with water. Thereafter, the air pressure above the sample was increased slowly to extrude the liquid from the sample and the permeability of water through the foam was determined to be 0.11 L/min/psi/cm².

Example 2

Reticulation of a Crosslinked Polyurethane Foam

Reticulation of the foam described in Example 1 was carried out by the following procedure: A block of foam measuring approximately 15.25 cm×15.25 cm×7.6 cm (6 in.×6 in.×3 in.) was placed into a pressure chamber, the doors of the chamber were closed, and an airtight seal to the surrounding atmosphere was maintained. The pressure within the chamber was reduced to below about 100 millitorr by evacuation for at least about two minutes to remove substantially all of the air in the foam. A mixture of hydrogen and oxygen gas, present at a ratio sufficient to support combustion, was charged into the chamber over a period of at least about three minutes. The gas in the chamber was then ignited by a spark plug. The ignition exploded the gas mixture within the foam. The explosion was believed to have at least partially removed many of the cell walls between adjoining pores, thereby forming a reticulated elastomeric matrix structure.

The average pore diameter of the reticulated elastomeric matrix, as determined from optical microscopy observations, was greater than about 275 µm. A scanning electron micrograph image of the reticulated elastomeric matrix of this example (not shown here) demonstrated, e.g., the communication and interconnectivity of pores therein.

The density of the reticulated foam was determined as described above in Example 1. A post-reticulation density value of 2.83 lbs/ft³ (0.0453 g/cc) was obtained.

Tensile tests were conducted on reticulated foam samples as described above in Example 1. The average post-reticulation tensile strength perpendicular to the direction of foam rise was determined as about 26.4 psi (18,560 kg/m²). The post-reticulation elongation to break perpendicular to the direction of foam rise was determined to be about 250%. The average post-reticulation tensile strength parallel to the direction of foam rise was determined as about 43.3 psi (30,470 kg/m²). The post-reticulation elongation to break parallel to the direction of foam rise was determined to be about 270%.

Compressive tests were conducted using specimens measuring 50 mm×50 mm×25 mm. The tests were conducted using an INSTRON Universal Testing Instrument Model 1122 with a cross-head speed of 10 mm/min (0.4 inches/minute). The post-reticulation compressive strengths at 50% compression, parallel to and perpendicular to the direction of foam rise, were determined to be 1.53 psi (1,080 kg/m²) and 0.95 psi (669 kg/m²), respectively. The post-reticulation compressive strengths at 75% compression, parallel to and perpendicular to the direction of foam rise, were determined to be 3.53 psi (2,485 kg/m²) and 2.02 psi (1,420 kg/m²), respectively. The post-reticulation compression set, determined after subjecting the reticulated sample to 50% compression for 22 hours at 25° C. then releasing the compressive stress, parallel to the direction of foam rise, was determined to be about 4.5%.

The resilient recovery of the reticulated foam was measured by subjecting 1 inch (25.4 mm) diameter and 0.75 inch (19 mm) long foam cylinders to 75% uniaxial compression in their length direction for 10 or 30 minutes and measuring the time required for recovery to 90% ("t-90%") and 95% ("t-95%") of their initial length. The percentage recovery of the initial length after 10 minutes ("r-10") was also determined. Separate samples were cut and tested with their length direction parallel to and perpendicular to the foam rise direction. The results obtained from an average of two tests are shown in the following table:

TABLE 2

| Time compressed (min) | Test Sample Orientation | t-90% (sec) | t-95% (sec) | r-10 (%) |
|---|---|---|---|---|
| 10 | Parallel | 6 | 11 | 100 |
| 10 | Perpendicular | 6 | 23 | 100 |
| 30 | Parallel | 9 | 36 | 99 |
| 30 | Perpendicular | 11 | 52 | 99 |

In contrast, a comparable foam with little to no reticulation typically has t-90 values of greater than about 60-90 seconds after 10 minutes of compression.

The measurement of the liquid flow through the material is measured in the following way using a Liquid permeability apparatus or Liquid Permeaeter (Porous Materials, Inc., Ithaca, N.Y.). The foam samples were between 7.0 and 7.7 mm in thickness and covered a hole 8.2 mm in diameter in the center of a metal plate that was placed at the bottom of the Liquid Permeaeter filled with water. The water was allowed to extrude through the sample under gravity and the permeability of water through the foam was determined to be 180 L/min/psi/cm² in the direction of foam rise and 160 L/min/psi/cm² in the perpendicular to foam rise.

Example 3

Histological Evaluation of a Plurality of Crosslinked Reticulated Polyurethane Matrix Implants in a Canine Carotid Bifurcation Aneurysm Model An established animal model of cerebral aneurysms was used to evaluate the histologic outcomes of implanting a plurality of cylindrical implants machined from a block of cross-linked reticulated polyurethane matrix as described in Example 2. The three animals were sacrificed at the three-month timepoint to assess tissue response to the cross-linked reticulated polyurethane matrix.

One of two different implant configurations was used in this experiment. The first configuration was a cylindrical implant measuring 6 mm diameter×15 mm length. The second configuration was a segmented, cylindrical implant measuring 3 mm diameter×15 mm length. To machine the implants, a rotating die cutter was used to cut 3 mm and 6 mm diameter cylinders. The implants were then trimmed to 15 mm in length. Implant dimensions were tested for acceptability by use of calipers and visualization under a stereo-microscope, with acceptance of implants measuring +/−5% of target dimensions.

An aneurysm was surgically created at the carotid arterial bifurcation of three dogs. This model simulates the hemodynamics of a human saccular aneurysm, which typically occurs at an arterial bifurcation. After one month, a second embolization procedure was performed in which a plurality of implants machined from a block of cross-linked reticulated polyurethane matrix was delivered into the aneurysm sac using a guide catheter. The 6×15 mm cylindrical implants were delivered using a commercially available 7 Fr Cordis Vista-Brite guide catheter. The 3×15 mm cylindrical implants were delivered using a commercially available 5 Fr Cordis Vista-Brite guide catheter. A loader apparatus was used to pull compress the implants from their expanded state into a compressed state for introduction through the hemostasis valve of the guide catheter. An obturator was then used to push the compressed implant from the proximal end of the guide catheter to the distal end, where the implant was deployed in a slow, controlled manner into the aneurysm sac.

A plurality of implants was used in each of the three dogs to achieve post-procedural angiographic occlusion as shown in Table 3 below. Platinum coil markers (0.003" diameter) embedded in the central lumen of the implants allowed the implants to be readily visualized under standard fluoroscopy, in order to verify implant deployment, placement, and positioning.

TABLE 3

| Dog # | Aneurysm Dimensions (mm) | Aneurysm Volume (mm³) | 6 × 15 mm Implants (n) | 3 × 15 mm Implants (n) |
| --- | --- | --- | --- | --- |
| BMX-1 | 22.4 mm L × 10.1 mm W | 1884 mm³ | 2 | 5 |
| BMX-2 | 18.9 mm L × 8.8 mm W | 1207 mm³ | 4 | 9 |
| BMX-3 | 23 mm L × 11 mm W | 2295 mm³ | 12 | 0 |

At three months following the embolization procedure, the animals were sacrificed to assess tissue response to the cross-linked reticulated polyurethane matrix. For histology processing, samples were dehydrated in a graded series of ethanol and embedded in methylmethacrylate plastic. After polymerization, each aneurysm was bisected (sawn) longitudinally by the Exakt method and glued onto a holding block for sectioning using a rotary microtome at 5-6 microns. The sections were mounted on charged slides and stained with hematoxylin-eosin and Movat pentachrome stains. All sections were examined by light microscopy for the presence inflammation, healing response, calcification and integrity of the wall at the neck interface and surrounding aneurysm.

Gross observation indicated that the aneurysm sac was fully packed with no open spaces. There was nearly complete pannus growth on the luminal surface at the proximal neck interface with focal, luminal invagination (pocket).

Figure 25:
FIGS. 25 and 26 represent micrographs of tissue ingrowth.
Figure 26:
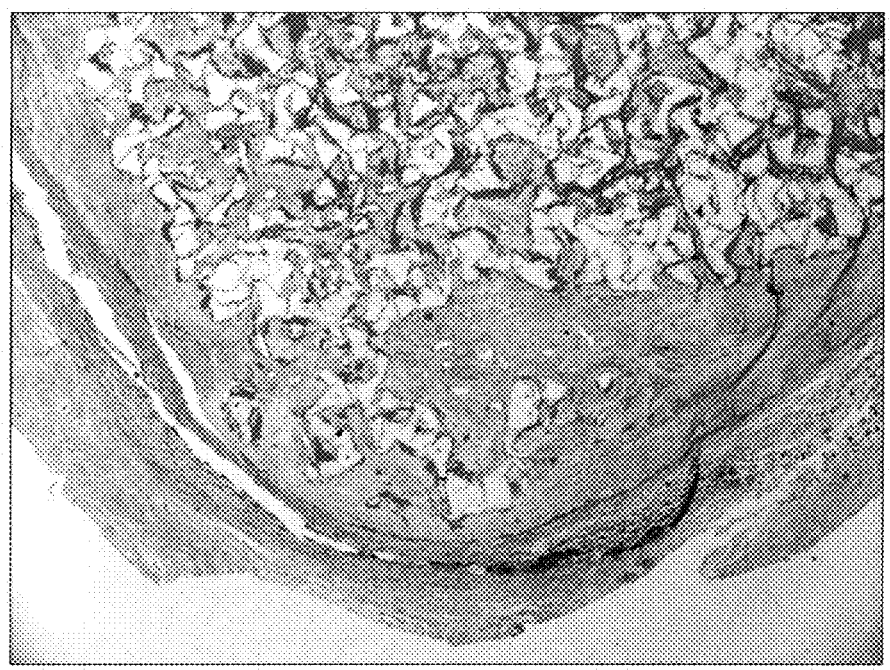

Longitudinal section through the proximal neck of the aneurysm showed greater than 95% luminal occlusion of aneurysm sac by reticulated polyurethane matrix. The luminal surface at the proximal interface showed almost complete covering by fibrous tissue with overlying endothelialization as shown in FIG. 25, which is 20× magnification showing fibrocollagenous tissue surrounding implant material and extending to luminal surface at proximal neck interface. There was nearly complete healing of tissue ingrowth surrounding the implanted material characterized by the presence of fibrocollagenous tissue (light-green and yellow by Movat Pentachrome stain) as shown in FIG. 26, which is a low power (4×) Movat stain of the apex of the aneurysm showing marked fibrocollagenous tissue ingrowth. There was minimal, focal organizing granulation tissue surrounding material (predominantly at the center of the occluded aneurysm) with mild, chronic inflammation consisting of lymphocytes and some giant cells, consistent with the healing response. There was almost complete replacement of elastic lamellae by fibrocollagenous tissue. No calcification was observed.

The histological response to the reticulated polyurethane matrix in this experiment demonstrated that the material can serve as a scaffold to support extensive organic tissue ingrowth with minimal inflammation and thereby holds promise as a bioactive solution to the treatment of cerebral aneurysms.

Example 4

Angiographic Outcomes from use of Reticulated Polyurethane Neurostring Implants in a Canine Carotid Bifurcation Aneurysm Model An established animal model of cerebral aneurysms was used to evaluate the angiographic outcomes of implanting a 0.030" Neurostring implants made from cross-linked reticulated polyurethane matrix as described in Example 2.

To create the Neurostring implants, thin sheets measuring 2.0 mm in depth were sliced from a block of reticulated polyurethane matrix. A sewing machine was then used to stitch surgical suture measuring 0.003" in diameter through the thin foam sheet to form a straight line. Individual strings were cut by using micro-scissors to trim around the suture line under a microscope until the final outer diameter of 0.030" (outside edge of the foam string) was achieved. Neurostring implant dimensions were tested for acceptability by delivering each individual string through a custom-made 3.5F (0.035" inner diameter) microcatheter. Platinum bands were hand-crimped every 1.0 cm along the length of each neurostring implants to impart radiopacity.

An aneurysm was surgically created at the carotid arterial bifurcation of three dogs. This model simulates the hemodynamics of a human saccular aneurysm, which typically occurs at an arterial bifurcation. After one month, a second embolization procedure was performed as follows. After preparing the access site using standard surgical technique, a 6F Boston Scientific Guide Catheter with Straight Tip was advanced to the aneurysm. A Boston Scientific Excelsior 3F Microcatheter was then advanced through the guide catheter into the aneurysm neck. One or two GDC-18 framing coils were then deployed through the microcatheter to frame the aneurysm. After positioning and detaching the framing coil, the Excelsior microcatheter was withdrawn. A custom-made 3.5F (0.035" inner diameter) microcatheter was then advanced through the guide catheter into the aneurysm neck. The Neurostring implant, loader, and pusher wire were removed from their sterile packaging. The loaded Neurostring implant and microcatheter were flushed with sterile saline. The loader/Neurostring implant was then introduced into the hemostasis valve of the microcatheter. The Neurostring implant was subsequently delivered into the aneurysm by pushing the implant with the pusher wire while using hydraulic assistance through the 3.5F custom microcatheter. The Neurostring implant was positioned and detached into the aneurysm. The pusher wire was removed from the microcatheter and an angiogram was performed to confirm occlusion. Neurostring implants ranging from 10-18 cm in length were deployed as necessary until angiographic occlusion was confirmed.

Table 4 below shows the quantities and volumes of framing coils and Neurostring implants used in each of the three animals. All 22 Neurostring implants were successfully delivered using hydraulic assistance and controlled mechanical detachment. Post-procedure angiographic occlusion was achieved in all three animals, with minor neck remnants.

TABLE 4

| Dog # | Aneurysm Dimensions | Framing Coil Qty | Total Neurostring Length (cm) | Number of Neurostring Implants |
|---|---|---|---|---|
| BMX-4 | 13.2 mm L × 12.1 mm W | 2 | 59.0 cm | 5 |
| BMX-5 | 14.0 mm L × 10.2 mm W | 1 | 100.5 cm | 8 |
| BMX-6 | 15.6 mm L × 10.2 mm W | 1 | 109.5 cm | 9 |

Figure 27A:
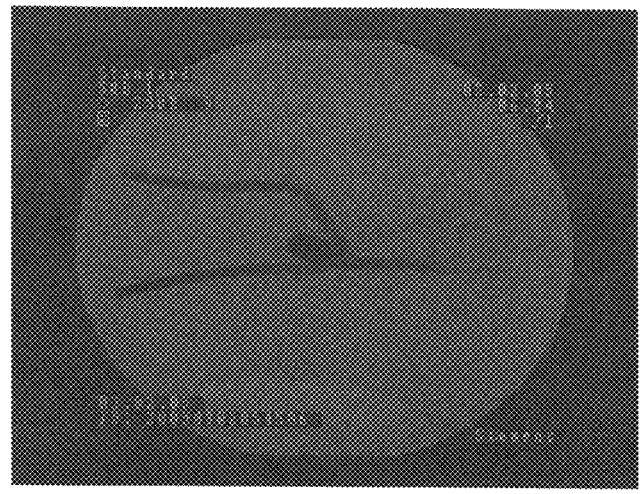
FIGS. 27A to 27C represent different stages of embolization formation in a dog.
Figure 27B:
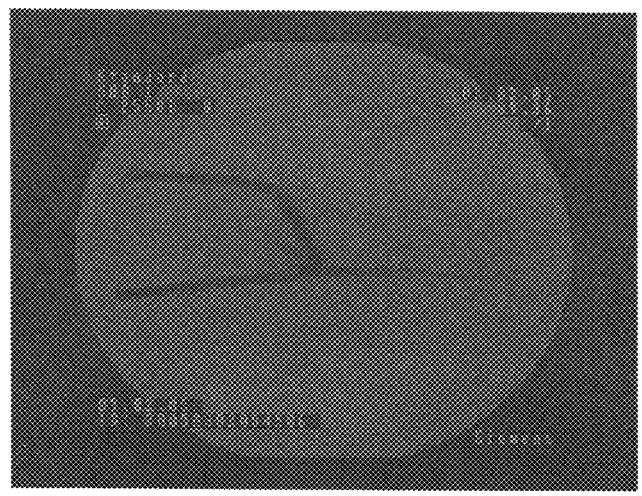
Figure 27C:
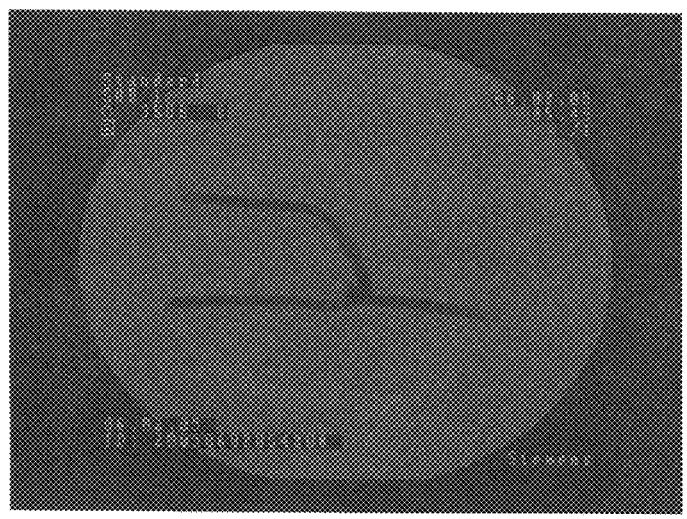

At two-week followup, an angiogram was performed to assess angiographic outcomes including device stability (compaction) and aneurysm recanalization. All three dogs showed stable or progressing occlusion with no device compaction and no evidence of aneurysm recanalization. The angiographic series from BMX-5 is shown in FIGS. 27A to 27B, where FIG. 27A represents pre-embolization, FIG. 27B represents post embolization, and FIG. 27C represents follow-up.

The angiographic outcomes at two-week followup demonstrated that Neurostring implants can be utilized for the embolization of cerebral aneurysms. This experiment showed the Neurostring device is consistently deliverable through a 3F microcatheter, and that the Neurostring implants are stable with no evidence of device compaction, no migration, and no aneurysm recanalization at the two-week followup timepoint.

Example 5

Effects of Packing Density on Angiographic Outcomes Using Reticulated Polyurethane Implants in a Canine Carotid Bifurcation Aneurysm Model An established animal model of cerebral aneurysms was used to evaluate the impact of different packing densities on angiographic outcomes for two different configurations of implants machined from a block of cross-linked reticulated polyurethane matrix as described in Example 2. The study evaluated the efficacy of different packing densities using (i) cylindrical implants (3 mm×15 mm, 6 mm×15 mm) machined as described in Example 3; and (ii) 0.030" Neurostring implants machined as described in Example 4. Packing density effectiveness was measured as angiographic occlusion and device stability (no compaction) at two-week followup.

Table 5 below shows that packing densities ranging from 40%-350% result in angiographic occlusion at two-week followup with stable or progressing occlusion and no device compaction. The one exception, BMX-1, was noted to occur in a dog with an unusual, giant, unstable aneurysm that continued to expand even at the two-week angiographic followup timepoint.

TABLE 5

| Dog # | Aneurysm Volume (mm³) | Packing Density (%) | Embolization Agents (Reticulated Matrix "RM" and/or GDC-18 Coils) | 2W Angiographic Outcomes vs. Baseline |
|---|---|---|---|---|
| PILOT | 1457.0 mm³ | 349.2% | 12-6 × 15 mm RM Cylinders | 100% occlusion No recanalization |
| BMX-1 | 1907.8 mm³ | 166.7% | 6-6 × 15 mm RM Cylinders 6-3 × 15 mm RM Cylinders | Recanalization |
| BMX-2 | 1196.3 mm³ | 115.2% | 2-6 × 15 mm RM Cylinders 5-3 × 15 mm RM Cylinders | Progressing thrombosis No device compaction |
| BMX-3 | 766.3 mm³ | 345.8% | 4-6 × 15 mm RM Cylinders 5-3 × 15 mm RM Cylinders | Stable occlusion No device compaction |
| BMX-4 | 1011.8 mm³ | 39.6% | 2-GDC-18 coils 59.0 cm RM Neurostring | No recanalization No device compaction |
| BMX-5 | 762.6 mm³ | 78.7% | 1-GDC-18 coil 100.5 cm RM Neurostring | Progressive occlusion No device compaction |
| BMX-6 | 849.7 mm³ | 76.6% | 1-GDC-18 coil 109.5 cm RM Neurostring | Progressive occlusion No device compaction |

This experiment demonstrated that various configurations of implants machined from reticulated polyurethane matrix can be utilized to embolize large aneurysms in a wide range of packing densities (40%-350%) with efficacious angiographic outcomes at two-week followup.

While illustrative embodiments of the invention have been described, it is, of course, understood that various modifications of the invention will be obvious to those of ordinary skill in the art. Such modifications are within the spirit and scope of the invention which is limited and defined only by the appended claims.

We claim:

1. An occlusion device for occluding a cerebral aneurysm comprising
   a member comprising a porous, explosively reticulated, elastomeric matrix, wherein the porous, explosively reticulated elastomeric matrix has at least partially removed cell walls between adjoining pores of the porous, explosively reticulated elastomeric matrix, and
   at least one longitudinally extending reinforcing filament,
   wherein the porous, explosively reticulated elastomeric matrix comprises a cross-linked, biodurable, reticulated, resilient elastomeric matrix comprising interconnected and intercommunicating networks of pores, channels, and voids, configured to permit ingrowth of tissue into the interconnected and intercommunicating networks of pores, channels, and voids,
   wherein the elastomeric matrix comprises polycarbonate polyurethane-urea, polycarbonate polyurea-urethane, polycarbonate polyurethane, polycarbonate polysiloxane polyurethane, or polysiloxane polyurethane, or a copolymers thereof, or any mixture thereof,
   wherein the elastomeric matrix is at least partially hydrophobic,
   wherein the device is configured to assume a non-linear shape that conformally fills a targeted vascular site, and
   wherein the device is configured to prevent recanalization and migration after tissue ingrowth has taken place in the reticulated matrix.

2. The device of claim 1, wherein there are two longitudinally extending reinforcing filaments.

3. The device of claim 2, wherein the reinforcing filaments are knotted or looped together at various points to secure the elastomeric matrix.

4. The device of claim 3, where the reinforcing filaments are knotted together by radiopaque bands.

5. The device of claim 2, wherein one longitudinally extending reinforcing filament comprises shape memory material and the other longitudinally extending reinforcing filament comprises radiopaque material.

6. The device of claim 5, wherein one longitudinally extending reinforcing filament comprises nitinol and the other longitudinally extending reinforcing filament comprises platinum.

7. The device of claim 6, wherein one longitudinally extending reinforcing filament is a nitinol wire and the other longitudinally extending reinforcing filament is a platinum coil.

8. The device of claim 1, wherein at least one reinforcing filament is radiopaque.

9. The device of claim 1, wherein the elastomeric matrix is formed from an isocyanate component comprising diphenylmethane diisocyanate, wherein the diphenylmethane diisocyanate is a mixture of 2,4'-diphenylmethane diisocyanate, 4,4'-diphenylmethane diisocyanate, polymeric MDI, and mixtures thereof.

10. The device of claim 1 which prevents recanalization and migration after tissue ingrowth has taken place in the reticulated structure.

11. The vascular occlusion device of claim 1,
wherein the longitudinally extending component is configured to be engaged with the member to secure the member and assist the device in conformally filling a cerebral aneurysm.

12. The vascular occlusion device of claim 11, wherein the member comprises resiliently compressible material.

13. The vascular occlusion device of claim 11, wherein each longitudinally extending component is selected from the group consisting of platinum wire, polymeric fiber or filament, a braid of platinum wire and polymeric fiber or filament, and a braid of two or more platinum wires.

14. The vascular occlusion device of claim 11, wherein there are two longitudinally extending components.

15. The vascular occlusion device of claim 14, wherein one longitudinally extending component comprises shape memory material and the other longitudinally extending component comprises radiopaque material.

16. The vascular occlusion device of claim 15, wherein one longitudinally extending component comprises nitinol and the other longitudinally extending component comprises platinum.

17. The vascular occlusion device of claim 16, wherein one longitudinally extending component is a nitinol wire and the other longitudinally extending component is a platinum coil.

18. The vascular occlusion device of claim 11 which prevents recanalization and migration after tissue ingrowth has taken place in the reticulated structure.

19. The occlusion device of claim 11, wherein the elastomeric matrix comprises polycarbonate polyurethane-urea, polycarbonate polyurea-urethane, polycarbonate polyurethane, or any mixture thereof.

20. The occlusion device of claim 1, wherein the elastomeric matrix comprises polycarbonate polyurethane-urea, polycarbonate polyurea-urethane, polycarbonate polyurethane, or any mixture thereof.

21. The occlusion device of claim 1, wherein the member comprises resiliently compressible material.

22. The occlusion device of claim 1, wherein the elastomeric matrix is free from a hydrogel.

23. The occlusion device of claim 1, wherein the elastomeric matrix is formed from a polyol component wherein the polyol component comprises polycarbonate polyol, polysiloxane polyol, poly(carbonate-co-siloxane) polyol, and mixtures thereof.

24. A packaging or introducer system comprising:
an occlusion device of claim 1.

25. The system of claim 24, further comprising an introducer sheath having a longitudinally extending lumen and proximal and distal ends;
a side arm attached to the proximal end of the introducer sheath and having a hemostasis valve and a flusher port; and
a pusher member extending through the hemostasis valve into the introducer sheath and having a distal end removably engaged to the proximal end of the occlusion device;
wherein the occlusion device is positioned within said lumen, said occlusion device having a proximal end; and
wherein an interlocking wire having a distal end extends longitudinally into the pusher member, the occlusion device has a loop at its proximal end, the distal end of the pusher member has an opening through which said loop extends, the distal end of the interlocking wire is releasably held within the distal end of the pusher member, and the distal end of the interlocking wire releasably engages said loop so that the distal end of the pusher member releasably engages the proximal end of the occlusion device.

26. The system of claim 25, wherein the distal end of the interlocking wire and the distal end of the pusher member are both radiopaque.

27. A method for occluding a cerebral aneurysm comprising:
introducing an introducer system of claim 24 into a delivery catheter having a longitudinally extending lumen and proximal and distal ends;
withdrawing the introducer sheath and side arm, leaving the occlusion device positioned within the lumen of the delivery catheter;
advancing the occlusion device using the pusher member to position the occlusion device within a targeted vascular site;
disengaging the pusher member from the occlusion device; and withdrawing pusher member.

28. An occlusion device comprising
a member comprising a porous, explosively reticulated elastomeric matrix, wherein the porous, explosively reticulated elastomeric matrix by explosion has at least partially removed cell walls between adjoining pores of the porous, explosively reticulated elastomeric matrix such that the explosively reticulated elastomeric matrix comprises interconnected and intercommunicating networks of pores, channels, and voids, and
at least one longitudinally extending component,
wherein the interconnected and intercommunicating networks of pores, channels, and voids are configured to permit ingrowth of tissue into the interconnected and intercommunicating networks of pores, channels, and voids,
wherein the device is configured to assume a non-linear shape that conformally fills a targeted vascular site.

29. An occlusion device comprising
a member comprising a porous, explosively reticulated elastomeric matrix, wherein the porous, explosively reticulated elastomeric matrix by explosion has at least partially removed cell walls between adjoining pores of the porous, explosively reticulated elastomeric matrix such that the explosively reticulated elastomeric matrix comprises interconnected and intercommunicating networks of pores, channels, and voids, and at least one longitudinally extending component, wherein the interconnected and intercommunicating networks of pores, channels, and voids is configured to permit ingrowth of tissue into the interconnected and intercommunicating networks of pores, channels, and voids, wherein the device is configured to be in a collapsed form and assume a non-linear shape in-situ within the aneurysm to conformally fill the aneurysm.

30. The occlusion device of claim 29, wherein the elastomeric matrix provides support and resilient compressibility enabling the device to be in the collapsed form for delivery to the aneurysm.

31. The occlusion device of claim 30, wherein the reinforcing filaments are knotted or looped together at various points to secure the elastomeric matrix, and wherein one longitudinally extending reinforcing filament comprises shape memory material and the other longitudinally extending reinforcing filament comprises radiopaque material.

32. The occlusion device of claim 29, wherein the elastomeric matrix comprises polycarbonate polyurethane-urea, polycarbonate polyurea-urethane, polycarbonate polyurethane, or any mixture thereof.

* * * * *